US012226333B2

(12) United States Patent
Dempers et al.

(10) Patent No.: US 12,226,333 B2
(45) Date of Patent: Feb. 18, 2025

(54) ORTHOPEDIC DEVICES AND SYSTEMS INTEGRATED WITH SENSORS AND CONTROLLING DEVICES

(71) Applicant: QUAZAR EKB LLC, Alpharetta, GA (US)

(72) Inventors: Ramon Dempers, Alpharetta, GA (US); Ophir Frieder, Chevy Chase, MD (US)

(73) Assignee: QUAZAR EKB LLC, Alpharetta, GA (US)

( * ) Notice: Subject to any disclaimer, the term of this patent is extended or adjusted under 35 U.S.C. 154(b) by 891 days.

(21) Appl. No.: 17/373,268

(22) Filed: Jul. 12, 2021

(65) Prior Publication Data

US 2021/0338469 A1 Nov. 4, 2021

Related U.S. Application Data

(63) Continuation-in-part of application No. 15/620,339, filed on Jun. 12, 2017, now Pat. No. 11,065,142.

(Continued)

(51) Int. Cl.
*A61F 5/01* (2006.01)
*A61B 5/00* (2006.01)
(Continued)

(52) U.S. Cl.
CPC .......... *A61F 5/0109* (2013.01); *A61B 5/0022* (2013.01); *A61B 5/02055* (2013.01); *A61B 5/1121* (2013.01); *A61B 5/296* (2021.01); *A61B 5/4836* (2013.01); *A61B 5/6812* (2013.01); *A61F 5/0111* (2013.01); *A61B 2562/0252* (2013.01); *A61B 2562/0261* (2013.01); *A61B 2562/0271* (2013.01); *A61F 2005/0144* (2013.01); *A61F 2005/0188* (2013.01)

(58) Field of Classification Search
CPC ................. A61F 5/0109; A61F 5/0123; A61F 2005/0188; A61B 17/135; A61B 17/1355; A61B 17/1325; A61B 17/1327; A61B 17/1322; A61B 17/132; A61H 2031/003; A61H 31/004; A61H 31/006; A61H 2011/005; A61H 11/02
See application file for complete search history.

(56) References Cited

U.S. PATENT DOCUMENTS 4,315,301 A 2/1982 Jimena
5,286,253 A 2/1994 Ficci
(Continued)

FOREIGN PATENT DOCUMENTS

WO WO 2006/016369 A2 * 2/2006

*Primary Examiner* — Camtu T Nguyen
(74) *Attorney, Agent, or Firm* — Pauley Erickson & Swanson

(57) ABSTRACT

An orthopedic support and/or treatment system including a brace, sleeve, and/or insert, comprising a power subsystem; a sensor subsystem; an adjustment mechanism; a software subsystem; a communication subsystem; and a telemedicine subsystem. The orthopedic treatment system includes and communicates over a network to a remote controlling device. The remote control device can be a computer, a mobile device, or any other controller. The sensor subsystem communicates to the remote control device, which in turn can be used to control the adjustment mechanism to adjust a tension or compression of the brace or sleeve.

16 Claims, 15 Drawing Sheets

Related U.S. Application Data

(60) Provisional application No. 62/351,586, filed on Jun. 17, 2016.

(51) Int. Cl.
    *A61B 5/0205*     (2006.01)
    *A61B 5/11*     (2006.01)
    *A61B 5/296*     (2021.01)

(56) References Cited

U.S. PATENT DOCUMENTS

| | | |
|---|---|---|
| 8,864,692 B2 | 10/2014 | Ingimundarson et al. |
| 2005/0080364 A1 | 4/2005 | Jensen et al. |
| 2008/0066343 A1* | 3/2008 | Sanabria-Hernandez .................. A43B 3/50 36/43 |
| 2010/0224198 A1 | 9/2010 | Ayuse et al. |
| 2012/0190989 A1 | 7/2012 | Kaiser et al. |
| 2012/0302821 A1 | 11/2012 | Burnett |
| 2013/0034512 A1 | 12/2013 | Bannister et al. |
| 2015/0125839 A1 | 5/2015 | Tillges et al. |
| 2017/0360586 A1 | 12/2017 | Dempers et al. |
| 2022/0409098 A1* | 12/2022 | McDaid ................ A61H 1/024 |

* cited by examiner

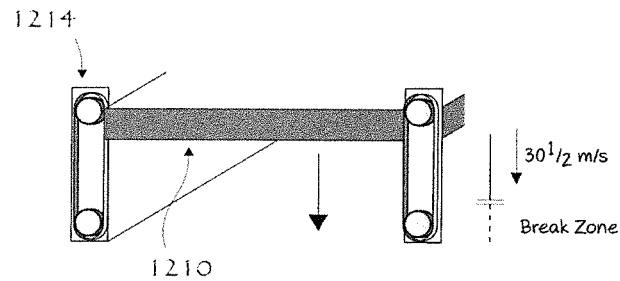
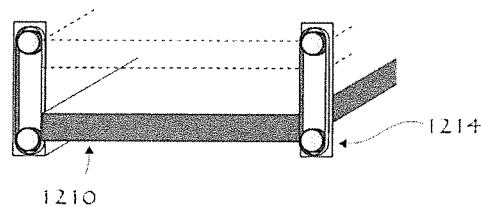
FIG. 29  FIG. 30
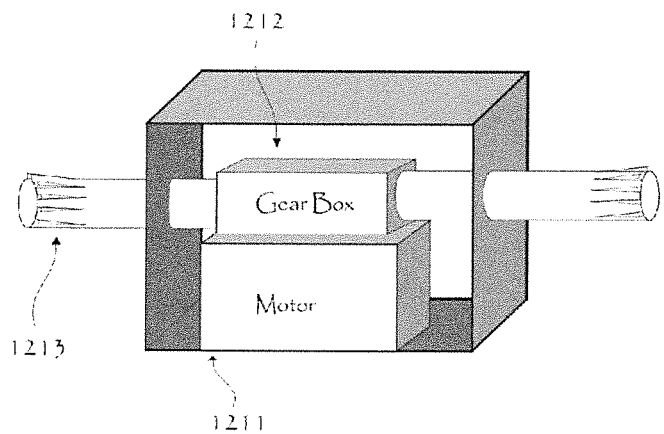
FIG. 31
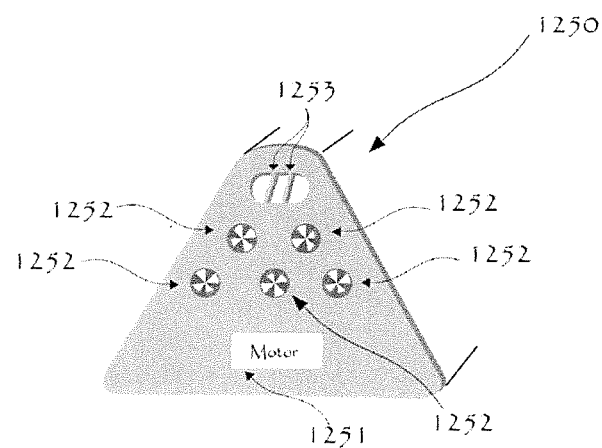
FIG. 32

ORTHOPEDIC DEVICES AND SYSTEMS INTEGRATED WITH SENSORS AND CONTROLLING DEVICES

CROSS REFERENCE TO RELATED APPLICATION

This application is a continuation-in-part of U.S. patent application Ser. No. 15/620,339, filed on 12 Jun. 2017, issued as U.S. Pat. No. 11,065,142, and which claims the benefit of U.S. Provisional Patent Application, Ser. No. 62/351,586, filed on 17 Jun. 2016. The parent Patent Application is hereby incorporated by reference herein in its entirety and is made a part hereof, including but not limited to those portions which specifically appear hereinafter.

BACKGROUND

Orthopedic treatment, namely physical therapy, pre-surgical, surgical, and post-surgical procedures, are affecting a continuously growing number of individuals. Regardless of the reason for this growth, be it sedentary lifestyle, heavy waste-line, increasing segment of aging population or any other reason, society must tackle and meet this growing demand for therapies that help individuals manage the health consequences of these trends.

Unfortunately, access to qualified orthopedic treatment facilities and personnel remains a concern. This is ever more so for remotely located and underserved population groups. To meet the clinical needs for orthopedic treatment for these groups, a significant advance would be orthopedic treatment methods incorporating "smart" technologies such as telemedicine and remote sensing technology.

However, despite advances in devices for orthopedic treatment, there remains a need for integrating "smart" technology to address the orthopedic treatment needs. Such technology should support automated feedback to assist the patient in their treatment cycle. There additionally is a continuing need to provide remote care for patients, providing the patients with easier access to their attending healthcare professional. Additionally, there is likewise a continuing need for providing the attending healthcare professional with management and diagnostic tools, thereby improving their ability to provide the highest of quality care for their patients, while driving down costs and improving convenience.

SUMMARY

This invention provides a support or treatment system for the body, a method implemented by the system, and encoded software instructions executable by the system for implementing the system and method. Embodiments of the system of this invention include a wearable device, embodied as any number of braces or sleeves for different parts of the body, such as sleeves and/or braces for support and/or treatment (e.g., athletic and/or medical) of, without limitation, ankles, legs, knees, hips, shoulders, necks, torsos, backs, hands, wrists, fingers, elbows, or combinations thereof. In embodiments of this invention, the wearable device, also referred to herein as an orthopedic device or a treatment device, is in communication over a network with a remote control device, typically including a data processor and a GUI for remote adjustment and/or monitoring of the wearable device.

Embodiments of this invention provide a support and/or treatment system including an orthopedic device adapted to be worn by a patient. The orthopedic device includes an adjustment mechanism and a control unit including a processor each integrated with the orthopedic device. The control unit is in controlling combination with the adjustment mechanism, such as to loosen or tighten components of the device. The system includes a control device remote from the orthopedic device and connected to the control unit over a network, such as to allow remote control and monitoring of adjustments and the results. A sensor subsystem is desirably integrated into the device to allow for the monitoring of the device and patient.

The invention further includes a support and/or treatment system including a brace or sleeve including a support structure and an interior cavity configured to receive a portion of a body. An adjustment mechanism is in combination with the support structure, wherein the adjustment mechanism adjusts a tension in at least a portion of the support structure. A control unit including a processor is integrated with the brace or sleeve and in control combination with the adjustment mechanism to adjust the tension of the support structure. A control device remote from the brace or sleeve is connected to the control unit over a network, such as to allow remote control and monitoring of adjustments and the results.

In embodiments of this invention the adjustment mechanism comprises a rotating bar or rod and two motors each at an opposing end of the rotating bar or rod and controllable by the control device via the control unit. The rotating bar or rod can include a flexible center section between two rigid end sections, and wherein the two motors are configured to rotate the rigid end sections in opposing rotational directions to twist the flexible center section to adjust the tension within the support structure. The adjustable rod can provide for adjustable tension in a joint support, and can be useful, for example, in reducing or eliminating hyper-flexing of a knee, such as after a knee replacement procedure.

In some embodiments of this invention, the adjustment mechanism further includes at least one, and desirably a plurality of straps each connected at a first end to the rotating bar or rod and fixed at a second end to the device, brace, or sleeve, wherein rotation of the bar tightens or loosens the straps to adjust a tension of or about an interior cavity of the device through which the body part(s) extend, thereby, for example, increasing a compression of the device on the body part(s).

In embodiments of this invention, the system includes a power subsystem; a sensor subsystem; a communication subsystem; a compression subsystem; a software subsystem; and a telemedicine subsystem. In presently preferred embodiments, the system further includes a remote control device. In various embodiments, the remote control device can be a computer (such as, workstation, personal computer, tablet, etc.), a mobile device (such as, a conventional or an intelligent cell phone) or any other controller. In some embodiments, the remote control device can be configured as part of the sleeve or brace, or alternatively, configured to communicate with the sleeve or brace.

Embodiments of the invention further include a support and/or treatment system, including an orthopedic footbed adapted to be worn by a patient. A footbed sensor is integrated with the orthopedic footbed, and configured to measure a load and/or weight thereon. A control device remote from the orthopedic footbed and connected to the footbed sensor over a network, and the control device is configured to measure and model stress in a foot, knee, and/or hip of the patient.

The footbed sensor can include an array of load cells in at least one of a heel location or a forefoot location of the orthopedic footbed. The array of load cells can be a quint (5) array, such as including four corner load cells about a center load cell. A low power wireless transmitter can be disposed within the orthopedic footbed, and in communication with the control device. The low power wireless transmitter can be configured to send readings to a connected smartphone and the smartphone comprising an application that stores readings locally and transmits the readings to a remote cloud server. A power subsystem can also be integrated with the orthopedic footbed, including a kinetic energy source configured to generate power from movement of the orthopedic footbed.

In embodiments of the invention, the orthopedic footbed comprises a brace or a sleeve configured to extend about a foot of the patient. A further sensor subsystem can be integrated with the orthopedic footbed or the brace or the sleeve, and in communication with the control device. Example sensor subsystems include a pulse sensor, a blood flow sensor, a blood pressure sensor, an oxygen sensor, a temperature sensor, an electric sensor, a moisture sensor, a biological/chemical sensor, a range of motion sensor, a compression/resistance sensor, a circumferential strain gauge, or combinations thereof. The sensor subsystem can be/include an electric sensor configured to determine muscular micro-electrical activity. The sensor subsystem can be/include a flexible ring integrated with the brace or sleeve and configured to be disposed about the foot, and at least one sensor adapted to measure swelling in the foot within the ring.

An adjustment mechanism can be/include a compression subsystem integrated with the brace or the sleeve and having variable tension controllable by the control device via the control unit. The compression subsystem can include a rotating rod and a motor configured to rotate the rotating rod to adjust a compression or tension in the brace or the sleeve. The compression or tension can be automatically monitored by the sensor subsystem and automatically adjustable by the control device.

The foot device can be used in concert with outer devices of this invention. The control device can communicates with the footbed sensor through a control unit of a second orthopedic device simultaneously worn on the patient. The second device can be a knee brace or sleeve including a support structure and an interior cavity configured to receive a knee of the patient, such as described above.

In one embodiment of the invention, the system includes: a first orthopedic device comprising a knee support brace adapted to be worn by a patient; a control unit including a processor integrated with the first orthopedic device; a telemedicine control device remote from the first orthopedic device and connected to the control unit over a network; an adjustment mechanism integrated with the first orthopedic device, wherein the control unit is in controlling combination with the adjustment mechanism, and the adjustment mechanism comprises a compression subsystem integrated with the first orthopedic device and having variable tension controllable by the telemedicine control device via the control unit, the compression subsystem comprises: a rotating bar or rod and a motor configured to rotate the rotating bar or rod to adjust a compression or tension in the first orthopedic device, and a plurality of straps each connected at a first end to the rotating bar or rod and fixed at a second end to the brace or sleeve, wherein rotation of the rotating bar or rod tightens or loosens the plurality of straps to adjust compression of the brace or sleeve about an internal cavity of the brace or sleeve; a sensor subsystem integrated with the first orthopedic device and in communication with the control unit, wherein the compression or tension is automatically monitored by the sensor subsystem and automatically adjustable by the control unit, and wherein the sensor subsystem comprises a first flexible ring integrated with the first orthopedic device, encircling the internal cavity of the brace or sleeve, and with at least one sensor adapted to measure swelling in a body part within the first flexible ring and the first orthopedic device; a second orthopedic device comprising an orthopedic footbed adapted to be worn by a patient; and a footbed sensor integrated with the orthopedic footbed, and configured to measure a load and/or weight thereon, wherein the telemedicine control device is remote from the second orthopedic device and connected to the footbed sensor over the network. The telemedicine control device is accessible by a remotely located telemedicine healthcare provider to receive metrics from the control unit and the footbed sensor, and for control and adjustment of the adjustment mechanism and the first orthopedic device throughout treatment of the patient by the telemedicine healthcare provider via the first orthopedic device.

The invention further includes a method of support or treatment using the orthopedic device described herein. The method includes one or more steps of: providing the orthopedic device to a patient, gathering data via sensors and the control unit of the device, automatically communicating the data to the remote control device, communicating operation instructions back to the control unit, and automatically adjusting a tension and/or compression in the device using the control unit and the adjusting mechanism. The method can include continual or periodic monitoring and communication, and repeating the reporting and adjustment steps as needed. The invention further includes encoded instructions for implementing the method steps, and appropriately partitioned and stored on recordable mediums of the control unit and/or the remote control device.

An additional embodiment of the sleeve of this invention is formed as an infant body suit. This suit in conjunction with the disclosed startle mechanism reduces the likelihood of suffering from SIDS.

To prevent SIDS, oxygen must steadily flow to the infant. As such, once a controller determines that the infant lacks oxygen, it triggers the disclosed startle mechanism(s) to startle and awaken the infant, typically resulting in the infant crying, and thus, forcing oxygen into the infant's lungs.

The disclosed method, device, and system relies on a sleeve-based body suit and a mobile, foldable, and/or tent-like encasement comprising of, but not limited to motors, fans, pulleys, platforms, paddings, puncture devices, heaters, coolers, and coverings. Although described via a series of specific illustrations, one skilled in the art will realize that many deviations of the described approaches are possible, and likewise, they too are covered under this disclosure.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in the specification and the appended claims, the term "orthopedic" is not intended to be limited to referring to medical care by a physician, and generally refers to any support, improvement, or treatment of one or more body parts, such as for medical treatment and/or improved performance (e.g., every day or athletic performance)

As used in the specification and the appended claims, the singular forms "a," "an" and "the" include plural referents unless the context clearly dictates otherwise. Thus, for example, reference to "a sleeve," "a controller," or "a rod" includes mixtures of two or more such functional sleeves, controllers, or rods, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

BRIEF DESCRIPTION OF THE DRAWINGS

The accompanying figures, which are incorporated in and constitute a part of this specification, illustrate several aspects and together with the description serve to explain the principles of the present disclosure.

FIGS. 29 and 30 illustrate a pulley system for an encasement, according to one embodiment of this invention.

FIG. 31 shows a power and drive mechanism for an encasement, according to one embodiment of this invention.

FIG. 32 shows an end of an encasement, according to one embodiment of this invention.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION OF THE DRAWINGS

The invention provides a support or treatment system that includes a support or treatment device in combination with a remote monitoring and/or controlling device. The support or treatment device can be any suitable orthopedic device, such as a brace or sleeve for one or more body parts. Exemplary sleeves or braces include, without limitation, prophylactic sleeves or braces, rehabilitative sleeves or braces, functional sleeves or braces, unloader/offloader sleeves or braces, splints, boots, supports, and immobilizers, with rigid exoskeleton and/or flexible support structures, for any one or more body parts, such as, without limitation, ankles, legs, knees, hips, shoulders, necks, torsos, backs, hands, wrists, fingers, or elbows. The remote control device can be a computer (such as a workstation, personal computer, tablet, etc.), a mobile device (such as a conventional or an intelligent cell phone) or any other controller communicating over a network. A local control device can additionally or alternatively can be configured as part of the device.

Figure 1:
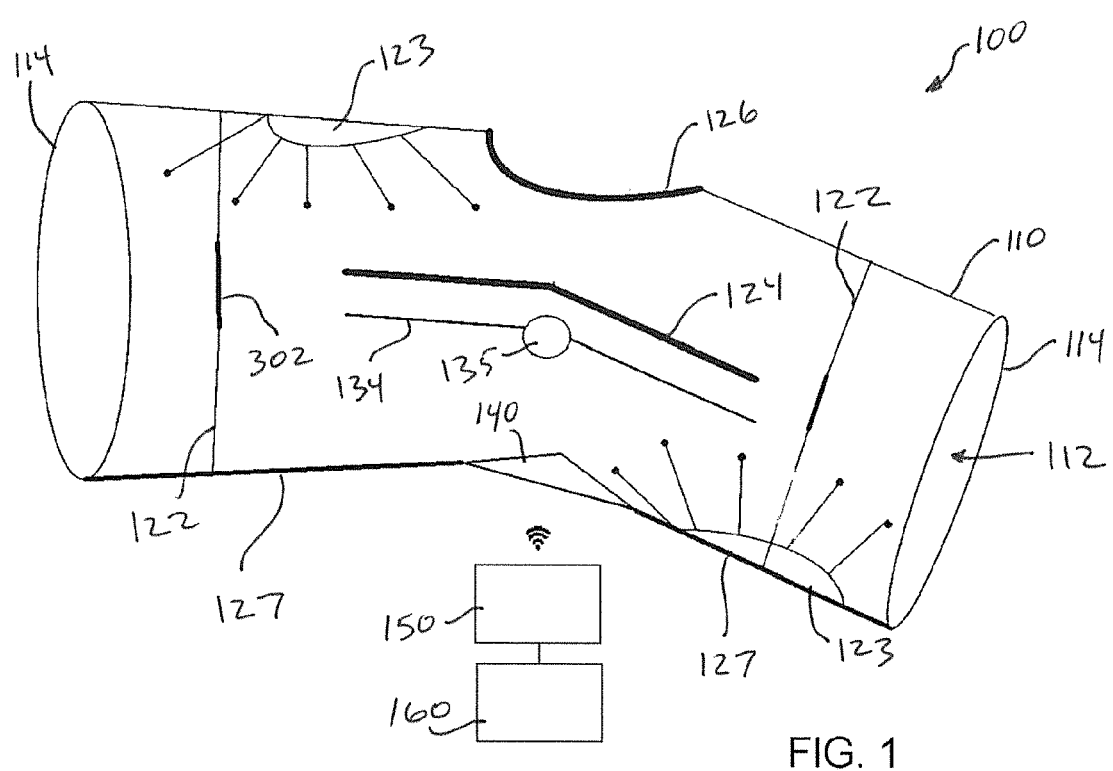
FIG. 1 illustrates a brace or sleeve according to one embodiment of this invention.

For purposes of illustration, FIG. 1 shows an exemplary orthopedic device according to one embodiment of this invention. The device 100 includes a support structure embodied as a sleeve 110, such as for a knee or elbow, having an internal cavity 112 accessible at either end by openings 114. The sleeve 110 is formed of any suitable material, such as a compression material or fabric to form a compressible sleeve for use with an injury at or near a knee or elbow joint of a subject. The sleeve 110 can be compressed according to embodiments of this invention in a manner that decreases the circumference of the sleeve and internal cavity, thereby providing compression to the surface of, for example, the thigh, knee, and/or calf.

In embodiments of this invention, the sleeve 110 includes a sensor subsystem of various sensing devices that interact via control devices with a software interface that is accessible to the subject and/or a remotely located healthcare provider such as a physician, physician's assistant, nurse practitioner, physical therapist, trainer, and the like. In some embodiments, the data from one or more sensing devices can be provided to the subject via a software interface hosted on a smart device such as a smart phone device wherein the data are transmitted to the smart device via a protocol such as Bluetooth or Wi-Fi standard protocols. The sensing devices incorporated into the sleeve can be selected based on the desired parameters to be followed for the specific application, e.g., sensors (including microsensor or nanosensor devices) can be incorporated that determine temperature, moisture, and specific materials to permit collection of data relevant to whether the subject has active inflammation, infection, or healing occurring at or near an injury or wound site encompassed by the sleeve 110. The data can also be transmitted using internet protocols via Wi-Fi or telephony protocols to a remotely located user such as a healthcare provider. It is likewise within the scope of this invention that the transmitted data are encrypted.

The orthopedic device of this invention desirably includes an adjustment mechanism integrated with the orthopedic device. The adjustment mechanism can include one or more adjustment devices or elements such as straps, rods, bars, and/or braces with variable tension, wherein the tension can be controlled by the user and/or a healthcare provider as required for a treatment protocol and/or based on data provided by one or more sensors on the orthopedic device. It is likewise within the scope of this invention that the tension is continuously monitored and computed on the orthopedic device using a resident software subsystem and is adjusted automatically in response data collected by the sensor subsystem.

Referring to FIG. 1, the sleeve 110 can be tensioned using an adjustment mechanism in combination with a sensor subsystem. In FIG. 1, resistance rod sensors 135 are placed as appropriate for the specific use of the orthopedic treatment system such that the one or more resistance sensors 135 determine and control a resistance rod 134 of the adjustment mechanism. In embodiments of this invention, the orthopedic treatment device, such as sleeve 110, can make use of a combination of resistance rod sensors and resistance rods made of composite materials to provide variable weight tension/resistance to the subject using the orthopedic treatment device. In embodiments of this invention, the torsion of composite fibers in a resistance rod can be increased, e.g., in a middle third of a resistance rod, via a micromotor or nanomotor device to provide stiffening of the resistance rods, and thereby, increasing tension for therapeutic benefit such as prehab and rehab for patients undergoing joint replacement surgery. An additional benefit to these patients is the ability to reduce the risk of hyperextension of the knee.

In various aspects, the disclosed orthopedic treatment system can be used by a patient or subject having various joint injuries, and provides structural support for the joint, such as during bending and/or flexing, using controlled (via the control device) resistance rods that facilitate patient rehabilitation. The sleeve includes controlled resistance rods that allows the user to gain strength in the joint being treated as well as rehabilitate the supporting musculoskeletal structures around the affected joint.

The brace or sleeve of this invention desirably tensions and releases tension components to provide the patient with highly controlled compression which is precisely controlled by a remote control device 160. Accordingly, healthcare providers can monitor the compression and set thresholds for each patient or groups of patients based on readings and/or other considerations as determined by their healthcare provider.

Accordingly, in various embodiments of this invention, healthcare providers can control, namely monitor and adjust the sleeve via either direct or indirect communication with the sleeve using a communication port in the controlling device. Therefore, providers are able to interact with the individual wearing the sleeve (namely, the patient) regardless of their geographic location. The healthcare provider can guide the patient using any known in the art methods. In various embodiments of this invention, such methods can include guidance via patient based metrics received via a telemedicine interface, e.g., a NetMetCare interface as described herein below. Communications can be accomplished via any network medium, namely, for example, over the Internet or cellular service.

The orthopedic treatment system of embodiments of this invention is used for rehabilitation and general treatment of injuries, such as to the knee, hip, shoulder, ankle, spine, wrist, or elbow. The orthopedic treatment system of this invention makes use of a unique set of sensors, power generation, power storage, strain gauges, and motors, and makes use of micro- and nano-technologies. The disclosed brace or sleeve component of the orthopedic treatment system is designed to be self-powered, waterproof, washable, and come in numerous sizes to support children, adults, and the elderly, thin, heavy set, to obese.

The disclosed orthopedic treatment system of embodiments of this invention includes an intelligent controller. With such a controller, the direct monitoring and alerting for specified conditions is supported. That is, the healthcare provider, e.g., a trained professional, friend, family member, acquaintance, or designee or even a computer program supporting artificial intelligence, can program the intelligent controller to detect any deviation from a desired condition. Such condition(s) can be, for example, without limitation, if the brace or sleeve is insufficiently exercised, the patient wearing the brace is perspiring or is simply too hot, or any other monitored conditioned. If a condition is detected, an alert can be triggered. As the communication between the healthcare provider and the patient wearing the sleeve is bidirectional, this alert can be immediately sent to any monitoring individual or device, and a responsive action, if appropriate, can be initiated.

Although the alert notification is primarily for the healthcare provider, it can likewise be of interest to the patient as in a form of a feedback loop. That is, such an alert can serve as a reminder to the patient to, for example, exercise as guidance for proper use, as reinforcement for moral support, positive feedback on meeting treatment goals, and the like, and other feedback as can be determined to be needed by a healthcare provider, subject, and/or manufacturer of the orthopedic treatment system.

Alerts according to embodiments of this invention include sending an alert to the user and their healthcare provider in the event the user is experiencing unexpected results from, for example, surgery. Additionally, the system can provide range of motion alerts to the user and healthcare provider alerting them to increase or reduce their exercise accordingly.

In embodiments of this invention, conditions can be detected via built in sensors in the brace or sleeve. In a further aspect, an alert can be triggered by the presence of moisture, such as from a discharge or drainage from a wound or surgical incision. For example, the sleeve can be configured with at least one moisture sensor. Such sensors can support surgery rehabilitation. Namely, the sensors monitor for any drainage from the incision and can alert both patient and healthcare provider as appropriate.

The brace or sleeve may likewise be configured with at least one biological or chemical sensor. For example, these sensors can be used to analyze any drainage from an incision. Such analysis can provide feedback to regarding biological or physiological status to the monitoring healthcare provider on the biological makeup of the drainage. Specifically, this feedback can significantly assist in surgery rehabilitation.

Using sensors, the brace or sleeve may likewise provide localized body temperature of the skin surface at or near a joint of a subject, e.g., the knee, and have appropriate upper and lower thresholds set. Alternatively, the sensor can provide data to assess time dependent trends or alterations in temperature. Additionally, through monitoring the trajectory of the temperature over time, the system provides early indications of a potential medical event. Note that it is within the spirit of this invention that not all versions of the sleeve are necessarily configured the same or with all specified components.

As discussed above, the readings from the sensors are desirably communicated to the healthcare provider. Thus, by using a virtual model of the portion of the body of the patient being treated along with the sensor readings obtained, an accurate representation of the patient's current physical condition can be provided to the healthcare provider. By introducing a potential treatment option to the model, the healthcare provider can simulate a potential reaction of the patient to the proposed option without actually subjugating the patient to that particular treatment option. Thus, multiple treatment scenarios can be analyzed with the best scenario being selected prior to initiating an actual treatment option for the patient. In doing such, the patient benefits from the best option without potentially suffering a non-optimal decision.

It is likewise within the scope of this invention to support and visualize longitudinal studies of the patient treatment and/or recovery process. More so, a comparison of other patients exposed to similar treatments can be provided to the healthcare provider. The mining of past outcomes can be incorporated into the treatment guidelines for the patient and their healthcare provider. Any of the many visualization approaches, and machine learning, data mining and/or inference approaches known in the art can be used to support the disclosed visualization and mining.

Also, it is likewise within the scope of this invention to configure a controller to control multiple simultaneous sleeves for one or more patients. In such manner, for example, a patient can wear multiple sleeves (on differing body parts) and the healthcare provider can be provided with reading from multiple sleeves forming a more complete understanding of the patient condition.

The system and device of this invention are suitable for both pre- and post-operative care as well for routine physical therapy, as well as many other uses such as physical training, sport performance improvement, prophylactic treatment, and the like. In FIG. 1, the sleeve is illustrated, without loss of generality, as a supportive gear for a human knee or elbow. However, in various aspects, using the same design, the disclosed sleeve, with appropriate size and shape modifications, is likewise can be used for treatment of a human hip, shoulder, spine, wrist, ankle, etc. The braces or sleeves of this invention make use of, depending on individual need, a unique set of sensors, stimulators, power generation, power storage, strain gauges, and motors. The devices desirably make use of micro and nano technologies, and can be designed to be self-powered, waterproof, washable, and/or available in multiple sizes. Multiple sizes may be needed to accommodate the varying age groups and body sizes of the target population, namely, youth, adults, and elderly, thin, heavy-set, and obese.

The overall design of the brace or sleeve includes one or more sensing devices, stimulators, rods, motors, power sources such as batteries, capacitors, or others known in the art, networks, and network interfaces. Exemplary sensing devices are or include sensors designed to detect and measure electrical, moisture, biological, temperature, pressure, sound inputs, etc. Stimulators include, without limitation, those designed to provide electrical, pressure, or puncture stimulation. The rods can be flexible and/or stiff and can be made from a diversity of materials such as metals, coils, wires, plastics, and fabrics. The motors can be of various types and sizes, their exact composition depending on their functionality requirements and availability as known in the state-of-the-art. The batteries can be potentially rechargeable and small, as known in the art, and can be configured to indicate low power capacity. Other, potentially rechargeable, power sources known in the art are likewise possible. Gears, gyroscopes, and coils, as known in the art, can likewise be used to generate and store energy and serve as a power source.

Figure 7:
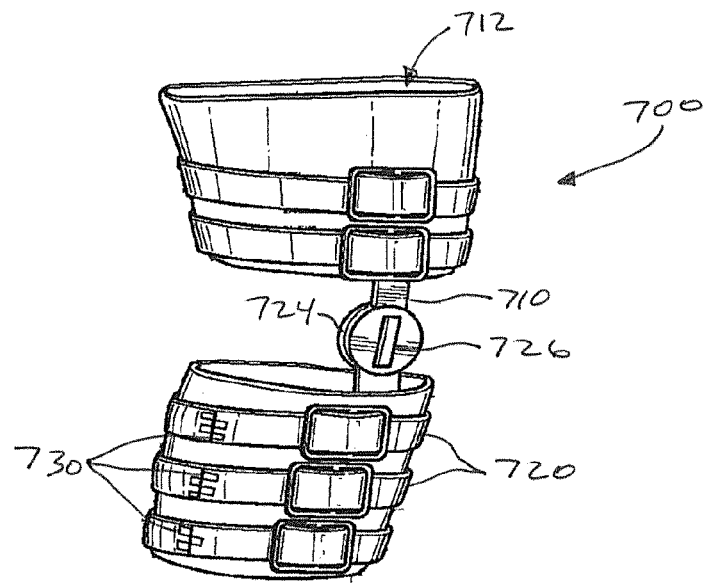
FIG. 7 illustrates a brace or sleeve according to another embodiment of this invention.

The body of the brace sleeve can include a mesh network that supports the components and communication and control of the configured components as needed. A network interface that receives instructions and transmits readings can be likewise included. Alternative device support structures can include a rigid support structure with adjustable tension joints and/or straps, such as shown in FIG. 7. Combinations of rigid and flexible materials are also possible, depending on need.

Referring again to FIG. 1, sleeve 110 is suitable as a knee joint brace or sleeve for a subject. It is understood that a subject can be a human. Alternatively, a subject can be a mammal, e.g., a horse or companion animal. In referring to FIG. 1, "orthopedic treatment device", "sleeve" and "brace" can be used interchangeably herein. As used herein, "brace" and "sleeve" can be used to refer to a same type of device, particularly as some devices have both brace and sleeve elements, or can refer to different types of devices, such as braces that incorporate hard shell components and, likely straps, versus sleeves formed of, for example, a fabric tube-like structure.

In FIG. 1, sleeve 110 comprises a control unit 140 to receive data from, operate, or otherwise control components of the device 100. In embodiments of this invention, the control unit 140 includes or is connected to a power source, a central processing unit with a corresponding operating system, a network controller, sensors, and a status panel. The control unit 140, and any related but separate component, is connected to the sleeve 110, such as fixed to the outer surface of the sleeve by any suitable connection and connectors.

Figure 2:
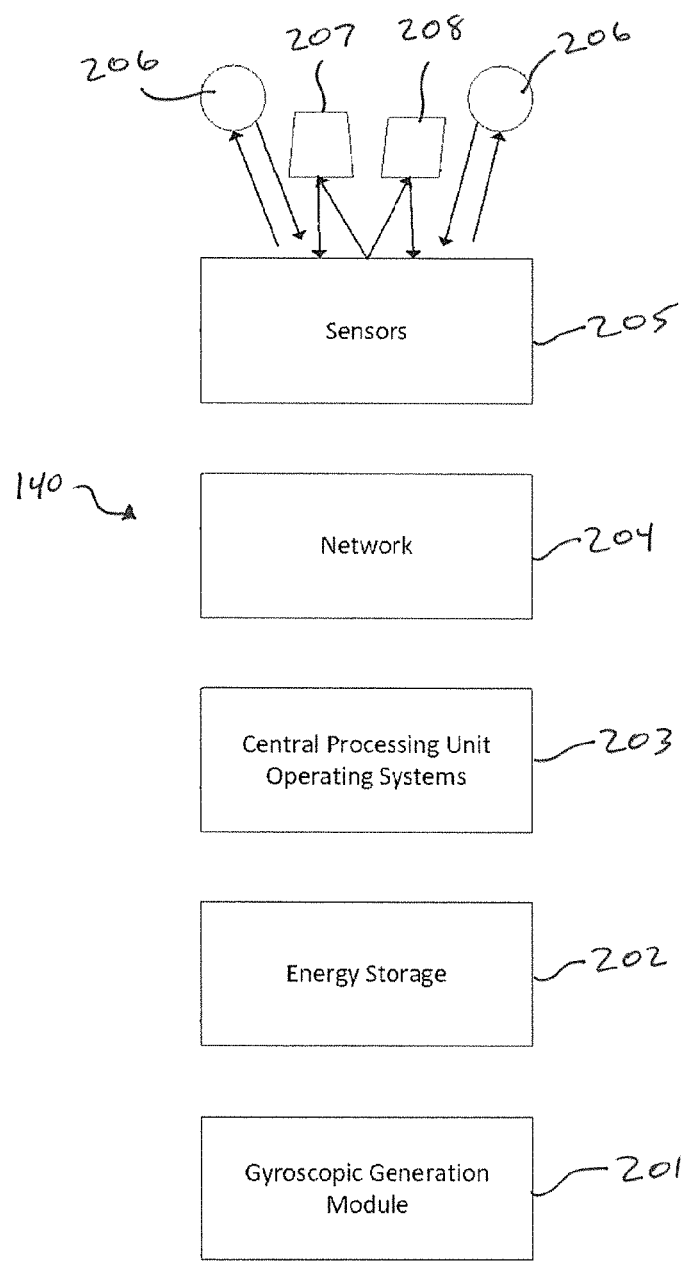
FIG. 2 shows a representative control unit according to one embodiment of this invention.

FIG. 2 generally and schematically illustrates a control unit 140 according to one embodiment of this invention. The control unit 140 includes a power source 201. The power source can be a self-generating source of power, such as via device motion using the illustrated gyroscopic generator module, which provides energy to an associated energy storage unit 202. Similarly, the power source 201 can be any other suitable energy source, e.g., a rechargeable battery unit. The placement of the power source for powering the operation of the device differs depending on what part of the body the device supports and depends on, but is not limited to, the motion or mobility of the joint and the characteristics and comfort of the wearer. In an exemplary embodiment for the knee, the power subsystem and power source 201 is placed in the arc of the cavity behind the knee, which provides a location that produces the energy to power the device through the flexing of the joint while the user goes about daily activities. This placement also provides a high level of comfort to the user as the power subsystem is 'hidden' out of the way behind the knee. In embodiments of this invention, the criteria for placement of the power subsystem on the wearer include one or more of, without limitation, the part of the body under treatment, the size (height and weight), age, gender, and comfort of the user, and the location that supports self-power generation if such feature is supported. That is, it is within the scope of this invention that either individually or in combination thereof self-generating and provided power, for example via a battery, provides the necessary power to fully operate the systems of the orthopedic device of this invention.

A central processing unit and a recordable medium with encoded instructions for a corresponding operating system 203 are likewise included and is powered by energy from the energy storage unit 202. In embodiments of this invention, any low power central processing unit (CPU), driven by an operating system (OS) known in the art can be used, e.g., a Raspberry Pi-based CPU. The CPU and OS control the global functioning of the sleeve 110, executing instructions and issuing commands as programmed. It is within the scope of the invention that the CPU and OS combination will include data encryption and decryption software, enabling the transmission of encrypted data.

The CPU 203 is in communication with a network controller 204 that provides transfer of data from readings and commands throughout the sleeve 110 to a remote control device, such as a smartphone or other controlling device. As discussed above, the remote control device can be a computer (such as, workstation, personal computer, tablet, etc.), a mobile device (such as, a conventional or an intelligent cell phone) or any other controller. In a further aspect, the remote controlling device can be configured as part of the sleeve or brace, or alternatively, configured to communicate with the sleeve or brace. Any low power network can be used for communicating with components on the sleeve. Communication with the remote device can be supported via any network technology or protocol known in the art, e.g., Bluetooth, wireless, Internet, and cellular, such as over a wireless signal accessible to the sleeve control unit 140 through a wireless router 150 shown in FIG. 1.

Further, the control unit 140 embodied in FIG. 2 likewise is connected to sensors of a sensor subsystem 205 integrated with the sleeve. The array of sensors measure, for example, temperature, moisture, electrical pulses, sound, and/or blood flow. Green light emitting diodes (LED) 206 visually monitor blood flow. The sensors monitor the blood flow in the main artery and vein of the recovering body part. Improper flow of blood from the heart (in the monitored artery) or from an extremity to the heart (in the monitored vein) can indicate poor circulation. When coupled with pulse readings obtained by the audio sensor 207, the blood pressure and temperature obtained by the coupler 208, poor circulation can be for example, an indicator of an arrhythmic condition. An inference engine running either on the local CPU 203 or on the remote device can suggest appropriate actions. Any suitable sensors are available for the sensor subsystem, including, without limitation, pulse sensors, blood flow sensors, blood pressure sensors, oxygen sensors, temperature sensors, electric sensors, moisture sensors, biological and/or chemical sensors, range of motion sensors, compression and/or resistance sensors, circumferential strain gauges, or combinations thereof.

Figure 3:
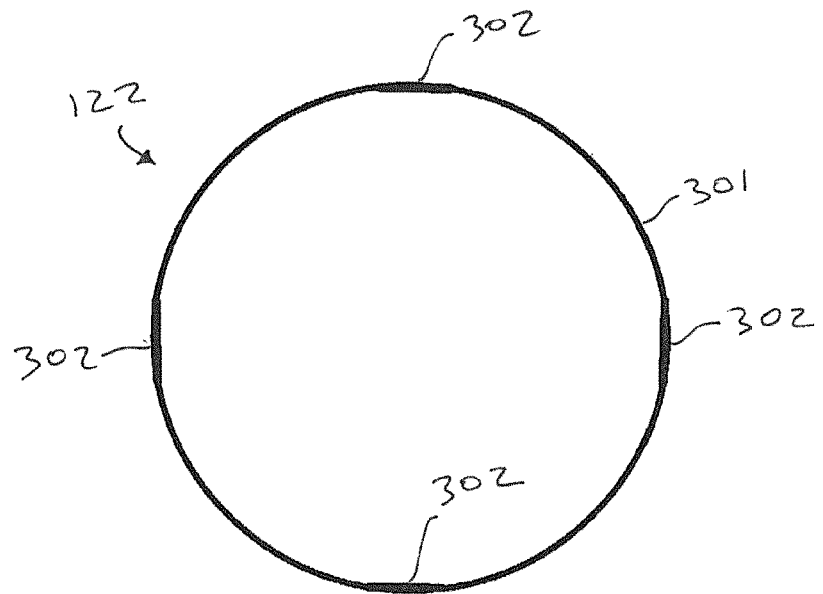
FIG. 3 shows a representative swelling detection ring according to one embodiment of this invention.

The sensor subsystem of FIG. 1 includes two flexible rings 122, one at or approximate each of two ends of the sleeve 110. The rings 122 can be oriented with one toward and about the thigh and one toward and about the calf, as shown in FIG. 1. These rings 122, shown in greater detail in FIG. 3, can be sensors used to determine the level of swelling surrounding the recovering body part, such as the knee. As shown in FIG. 3, a non-limiting four sensors 302 measure the pull (hence circumference) of the attached cable 301. By measuring the circumference, the precise level of swelling is noted. Although four sensors 302 are shown, it is within the scope of this disclosure to have a greater or smaller number of sensors. Any suitable sensor, such as a strain gauge, can be used to form the rings 122.

In an aspect, the sleeve 110 of FIG. 1 can contain an assortment of sensor(s) and stimulator(s) 123 in multiple positions. In various aspects, these sensor(s) can measure a diversity of inputs such as moisture, electric current, and sound. The data signal or information derived from such inputs, like with other components in the orthopedic treatment system, can be sent via a network to the CPU for further processing. The stimulators send pulses to simulate the body part under care. Stimulation targets to invoke body responses to be measured, provide treatment, or to serve as a form of reminder.

Figure 4:
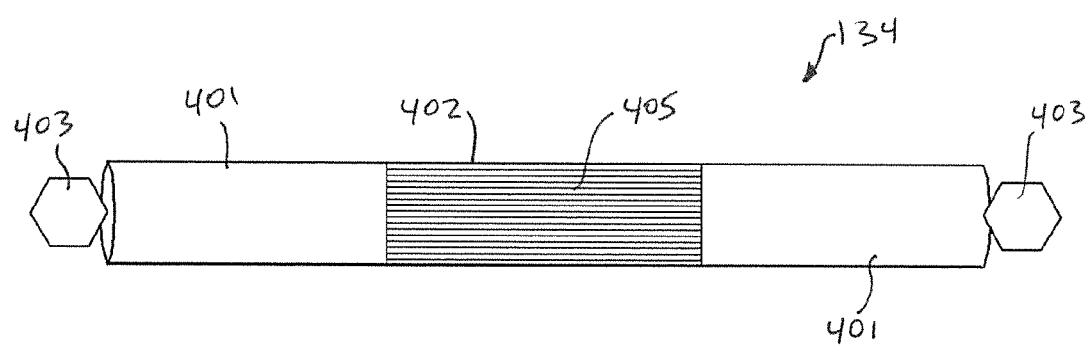
FIG. 4 shows a representative resistance rod according to one embodiment of this invention.

FIG. 4 shows an exemplary resistance rod 134 integrated with the sleeve, such as on opposing sides of, or at other predetermined placements about, the interior cavity, and designed to flex in the direction of, and along with, the enclosed joint. The rod 134 of FIG. 4 includes two rigid sections 401, one at each end, and a center section 402 that is flexible. The center section 402 can be tightened or loosened so as to stress or release the tension of the rod 134. In embodiments of this invention, a nano motor 403 is attached to each rigid section of the rod as shown. The motors can rotate in counter directions to each other, i.e., one clockwise the other counter-clockwise. For example, rotating the motors in one pair of opposing directions can tighten the rod; and reversing the rotation of both motors can loosen the rod. It is within the scope of this invention that either motor rotate in either direction to tighter or loosen the rod as long as they rotate counter to each other. In embodiments of this invention, the middle section is formed of unidirectional stranding of composite fibers 405 to provide the flexibility and torsional tightening. Exemplary composite fibers include monofilament carbon fibers that collectively tighten with or against each other when twisted, somewhat analogous to the tightening of a braided rope when twisted.

As shown in FIG. 1 alongside one or more of the rods 134 an array of sensors 124 can likewise be included on or in the sleeve 110. This array 124, like the other sensors, records readings and sends them to the control unit 140 for further processing. In particular, this array of sensors 124 measures the range of motion exhibited by the body part under treatment.

In some embodiments of this invention, such as shown in FIG. 1, a biological sensor 126 is included in or on sleeve 110. The sensor 126 can perform a biological or chemical analysis of the seepage surrounding an incision or wound. For example, the sensor itself conducts a chemical analysis of a substrate present in the seepage from an incision or wound. Any such chemical analysis known in the art can be used. It is likewise within the scope of this disclosure that the analysis is conducted by multiple components. More so, it is within the scope of this disclosure that the biological sensor 126 is placed in multiple places within the sleeve 110. Results of the biological analysis can be communication to the control unit 140.

Figure 5:
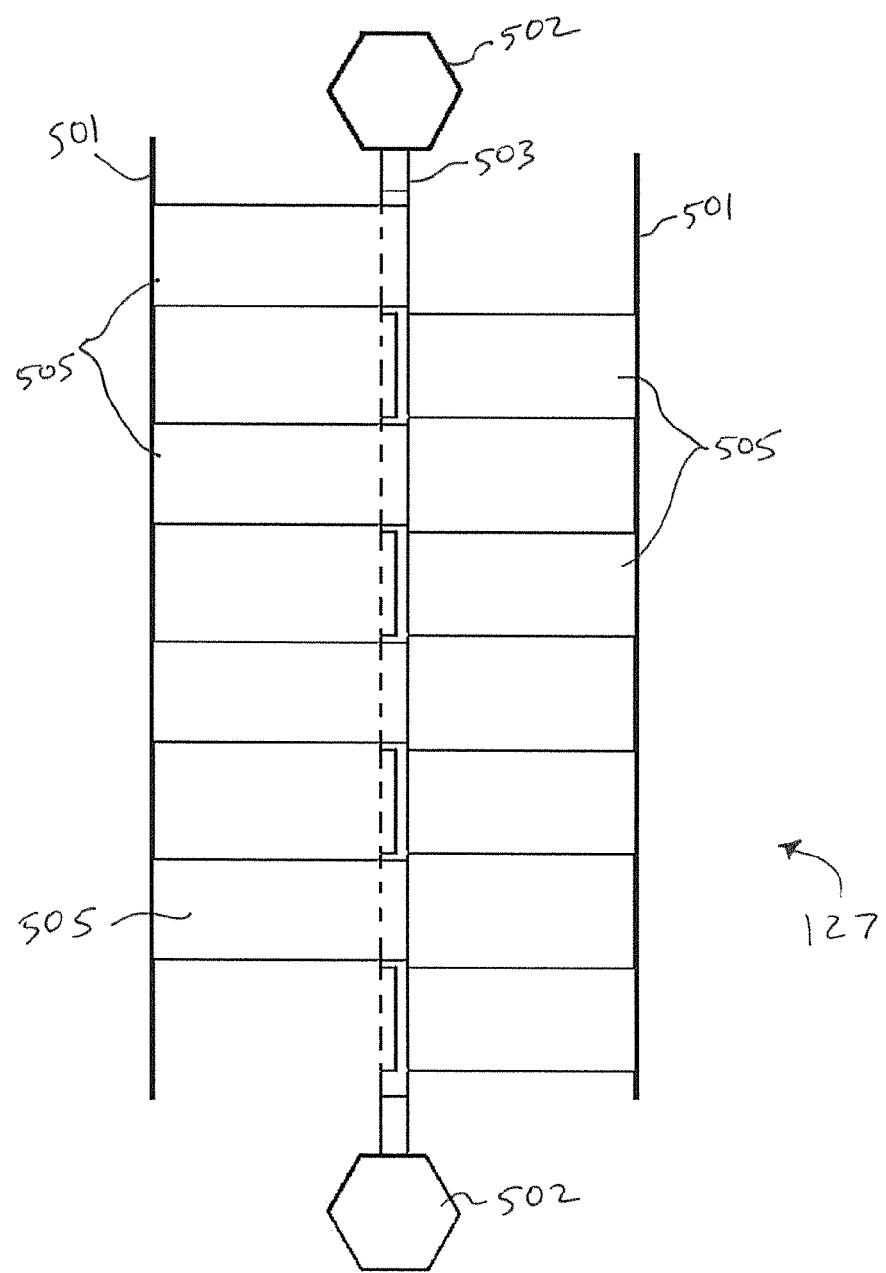
FIG. 5 shows a representative adjustment mechanism according to one embodiment of this invention.

The adjustment mechanism of this invention can additionally or alternatively include a compression subsystem that provides a tightening and loosening functionality through all or one or more sections of the orthopedic device. FIG. 1 shows a compression subsystem with compression structures 127 on each end of the sleeve 110. FIG. 5 shows an exemplary compression structure 127 according to embodiments of this invention. The compression structure 127 includes, along a section of the sleeve 110, a pair of spaced apart bars 501 that can be secured to the sleeve by threads, flaps, or other suitable means. Straps 505 are attached to and between one of the respective bars 501 and a central rotating bar 503 controlled by motors 502 can be used to tighten and loosen the compression structure, and thus the sleeve. The motors 502 rotate in a same direction, and the straps 505 either tighten the sleeve 110 by wrapping themselves around the rotating bar 503 and pulling the bars 501, or loosen the sleeve 110 by unwrapping themselves from the rotating bar 503. Thus, pressure can be exerted on the healing body part, as needed and controlled by the remote control unit. Various and alternative sizes, shapes, and configuration are available for the compression structures, bar, straps, and rods, depending on need. For example, only one bar may be needed, or the straps can be directly attached or integrated to the sleeve without the bars.

Figure 6:
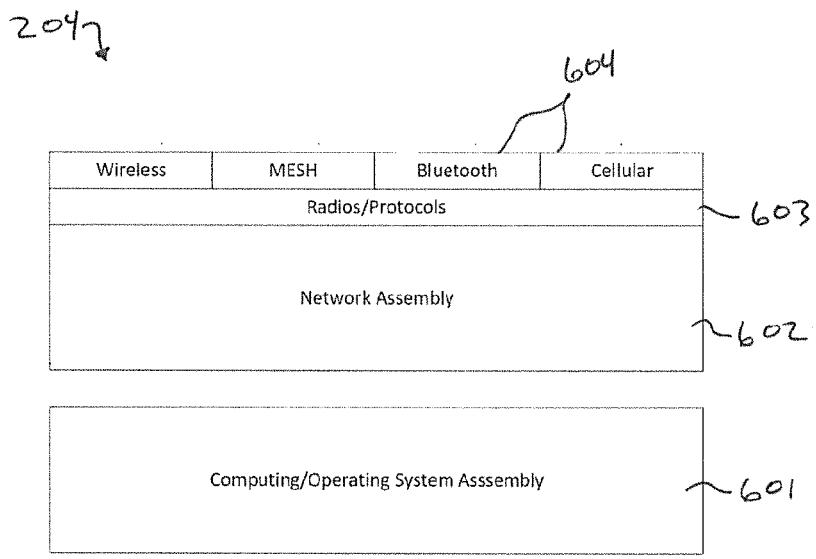
FIG. 6 shows a representative network controller mechanism according to one embodiment of this invention.

FIG. 6 illustrates an exemplary network controller unit 204 comprising various subunits such as an operating system subunit 601, a network assembly subunit 602, a radio/protocol subunit 603, and/or one or more network communication subunit 604. The network controller 204 can be located within control unit 140 or an assembly thereof. In embodiments of this invention, the control unit 140 includes a computing unit running an operating system subunit 601 to support the network communication flow controlled by the network controller 204. Network configuration details can be maintained in the network assembly subunit 602. Protocol specifications can be maintained on a radio/protocol subunit 603 for one or more network communication subunit 604, such as wireless, mesh, Bluetooth, and cellular networks. Some of the network communication subunits can communicate with one or more of the components on the sleeve, e.g., a sensor or motor device; whereas other network communication subunits can communicate with a remote device. It is within the scope of this invention to support additional or alternate network types as known in the art. It is likewise within the scope of this invention to integrate both logically and/or physically the functionalities of the above components into fewer components or to partition them across a greater number of components.

FIG. 7 shows an exemplary orthopedic device 700 according to one embodiment of this invention. The device 700 includes a support structure with a jointed rigid knee brace 710. Straps 720 and comfort sleeves 730 form an internal cavity 712. A joint pivot 724 can be integrated with a resistance rod 726, such as discussed above for FIG. 4. One or more of the strap 720 can be tightened according to embodiments of this invention, such as with a compression mechanism 730 similar to shown in FIG. 5, in a manner that decreases the circumference of the straps 720 and internal cavity 712, thereby providing increased support and/or compression to the surface of, for example, the thigh and/or calf In embodiments of this invention, all readings collected can be stored in a database. Any database management system known in the art can be used. The sleeve periodically (logically continuously) records and transmits readings; thus, the database can store these readings creating an individual longitudinal history. By utilizing any alerting or triggering monitoring approach known in the art, conditions of significant interest for patient care can quickly be detected, and the supervising healthcare professional can be alerted. More so, by using any trend detection approach known in the art, even minor fluctuations or conventional readings that normally would go undetected can be noted if they are part of a trend of interest. For example, a continuous slight increase in temperature might indicate infection if this reading is sustained for a prolonged period of time.

Patient treatment history can be visualized. The treating healthcare professional can request varying charting and presentation visualization displays of the stored history. Additionally, using patient treatment models, models potentially using input parameters stored in the database that can be patient specific, a variety of potential treatment options can be considered. For example, contraction of the sleeve might be considered, and the model might suggest possible reactions of the patient should these contractions be activated. Thus, various treatment options can be attempted, and the best option selected without subjecting the patient to unnecessary and potentially unhealthy approaches.

The following exemplary components can be used to implement a non-limiting aspect of the disclosed invention. It is within the scope of this invention, however, to use any known in the art technologies to support the components to implement the disclosed sleeve. The components can comprise a power source, a sensor, a communication subsystem, a computation subsystem, e.g., a CPU, and a compression subsystem. It is likewise within the scope of this disclosure to integrate both logically and/or physically the functionalities of the above components into fewer components or to partition them across a greater number of components.

In various embodiments of this invention, exemplary components include: power subsystem; sensor subsystem comprising six primary sensors (temperature sensor, electric sensors, moisture, biological, and chemical sensors, range of motion sensors, resistance rod sensors, and circumference measurement sensors); communication subsystem; compression subsystem; motor assembly; software; and telemedicine support.

1. Power Subsystem

In embodiments of this invention, the orthopedic treatment device includes a power subsystem. In some embodiments, such as illustrated in FIG. 2, the power subsystem includes a generator based on gyroscopic and inertial components 201, that generates voltage and amperage (VA) via internal motion and the energy so generated is stored in a kinetic energy storage unit (KESU) 202. In a further aspect, the power subsystem can comprise a micro-wiring harness for distributing power to the various devices in the sleeves.

2. Sensor Subsystem

In some embodiments, the sensor subsystem can include one or more of the following primary subcomponents: temperature sensor; electric sensors; moisture, biological, and chemical sensors; range of motion sensors; resistance rod sensors; and circumference measurement sensor. The primary subcomponents can be microscale or nanoscale sensor devices. The sensor subsystem can further include other subcomponents as determined by the needs or requirements of a healthcare provider and/or subject.

a. Electric Sensor

The sensor subsystem can include one or more electric sensor(s). The electric sensor(s) can be located within or on one or more pads located within or on the orthopedic treatment device. As shown in FIG. 1, without limitation, a plurality of sensors 123, such as bioelectrical sensors, can also be located within or on two pads located within or on the sleeve 110. The electric sensors can be placed on the orthopedic treatment device such that electrical impulses in, for example, the thigh and calf of the subject can be determined.

The electric sensor(s) desirably determine(s) muscular micro-electrical activity. The micro-electrical activity data can be used to determine recovery status of one or more muscles, i.e., a method of measuring the health status of a muscle. In some embodiments of this invention, the micro-electrical activity data can be used to determine parameters useful for a prehabilitation protocol. For example, in a subject undergoing prehabilitation therapy, the micro-electrical activity within the muscle can be used to assess the level of stress placed upon one or more muscle, and thus, can be used to determine the exercise level that a subject is exerting. It is understood that prehabilitation, or alternatively referred to in the art as "pre-hab," refers to a form of strength training, aims to prevent injuries before the actual occurrence. Since rotator cuff and elbow injuries, among other things, are common among athletes in a wide range of sports, training the muscles surrounding these vulnerable joints can prevent injuries sustained from repeated wear and exertion.

b. Range of Motion Sensor(s)

The sensor subsystem can include one or more range of motion sensors. As seen in FIG. 1, the range of motion sensors 124 can be placed as appropriate for the specific use of the orthopedic treatment system such that a range of motion can be determined. The range of motion sensors can use various techniques known in the art to measure the movement of the joint to determine the range of motion in the joint.

In some embodiments the orthopedic treatment system comprises at least two range of motion sensors located such that the range of motion specific to the area of the body being treated can be determined, e.g., the range of motion that a subject can provide between the upper and lower arm wherein the orthopedic treatment device is designed for treatment of an elbow, or alternatively, the range of motion that a subject can provide between the upper and lower leg wherein the orthopedic treatment device is designed for treatment of a knee. For example, in an orthopedic treatment system for the knee, the range of motion sensor can measure the range of motion through the arc in which a knee travels. In one embodiment, the orthopedic treatment system is designed for use with a knee injury and comprises two range of motion sensors.

As another example, for an orthopedic treatment system for the hip, the range of motion sensor can measure both the arc of motion and rotation at the hip. In a still further non-limiting example, an orthopedic treatment system for the shoulder, the range of motion sensor can measure both rotation at or around the shoulder and the forward back arc motion. In various embodiments, the joint range of motion that is measured is dependent upon the joint or body region for which the orthopedic treatment system is utilized, and sensor placement and number can be determined by the skilled artisan to provide more or less plane through which they measure the joints action.

c. Moisture, Biological, and Chemical Sensors

The sensor subsystem comprises moisture, biological, and/or chemical sensors. The moisture, biological, and/or chemical sensors can be placed on the device as appropriate for the specific use of the orthopedic treatment system. For example, as shown in FIG. 1, the orthopedic treatment system is designed for use with a knee injury and the moisture, biological, and chemical sensors 126 are placed at or near a knee opening in the middle front of the sleeve 110 to allow these sensors 126 to measure the moisture, biological material and/or chemical material being emitted at or near the site of placement. In this example, the moisture, biological, and chemical sensors 126 can detect potential infection or seepage from a wound.

d. Resistance Rod Sensor(s)

The sensor subsystem comprises one or more resistance rod sensor(s) placed as appropriate to determine and control a resistance rod, such as rod 134 in FIG. 1. In embodiments of this invention, the orthopedic treatment device can make use of a combination of resistance rod sensors and resistance rods made of composite materials to provide variable weight resistance to the subject using the orthopedic treatment device. The torsion of unidirectional stranding of composite fibers 405 in a resistance rod can be increased, e.g., in the middle third 402 of resistance rod 134, via a micromotor or nanomotor device 403 to provide stiffening of the resistance rods and thereby increasing resistance. In embodiments of this invention the orthopedic treatment device can include two resistance rods wherein each rod can be controlled separately. In another embodiment, the orthopedic treatment device can include a plurality of resistance rods distributed as appropriate around the central axis of the inner cavity and joint, with each resistance rod subject to independent control. The number and distribution of the resistance rods around a joint axis can be determined by a healthcare provider as appropriate to the joint, type of injury, and rehabilitation algorithm.

e. Temperature Sensor(s)

The sensor subsystem can include a temperature sensor, such as located on the back of the orthopedic treatment device. In a further aspect, the temperature sensor, such as a thermocouple sensor 208, is placed such that it senses the subject's body temperature behind the knee through direct contact with the skin.

f. Circumference Measurement Sensor(s)

The orthopedic treatment device comprises one or more circumference measurement sensors 302, such as including at least one multi-sectional strain gauges that provides circumference measurements relative to the central axis of the joint or area of the body for which the orthopedic treatment device is being used to treat. In embodiments of this invention, the measurements can be calculated in four parts, which help determine swelling in the region and the "shape" of the swelling. Shape distortions describe mathematically how the swelling is manifested, in other words in which region of the extremity the swelling is occurring.

3. Communication Subsystem

In embodiments of this invention, the orthopedic treatment device includes a communication subsystem. The specific communication protocol or modality used can be any appropriate to the desired end use, taking into account the preferred communication protocol or modality used by the healthcare provider and/or subject using the orthopedic treatment device that allows for directional communication of data and instruction between the orthopedic treatment device and an external user, e.g., a healthcare provider and/or a subject using the device. For example, the communication subsystem can comprise one or more of the following communication platforms MESH, Bluetooth, 3G, 4G, 4G LTE, 4G LTE+, 10 MB, 100 MB, 1 GB and higher wireless and future networking protocols. In a further aspect, the communication subsystem can comprise TCP/IP, ZIG-BEE 3.0 and above; Z-Wave standards or any future communications protocols suitable to the operation of the device. Similarly, the data communicated can be encrypted.

4. Compression Subsystem

In embodiments of this invention, the orthopedic treatment device includes a compression subsystem. For example, as shown in FIGS. 1 and 5, the compression subsystem can include three core components: a woven compression support structure matrix; a flexible worm drive assembly; and a motor assembly. The woven compression matrix can comprise a series of interleaved fabric panels or straps 505 that can be pulled together or apart to increase or decrease pressure on a joint being treated. The flexible worm drive assembly 503 allows the device to adjust the compression of the orthopedic treatment device, i.e., as the worm moves through one full rotation it either releases or tightens the woven compression matrix.

5. Software Subsystem

In embodiments of this invention, the orthopedic treatment device comprises a software subsystem supporting bidirectional communication with various computing device platforms. In a further aspect, the software subsystem comprises a software system residing on the orthopedic treatment device that communicates data obtained from sensors on or within the orthopedic treatment device to a software system residing on a remote controlling device such as a mobile device platform, a tablet device platform, a laptop computing device platform, a desktop computing device platform, a cloud computing platform, a web appliance computing platform, and the like, or a combination of such computing platforms. In a still further embodiment, the software subsystem comprises a software system residing on the orthopedic treatment device that receives instructions from a software system residing on a remote control device such as a mobile device platform, a tablet device platform, a laptop computing device platform, a desktop computing device platform, a cloud computing platform, a web appliance computing platform, and the like, or a combination of such computing platforms.

In a further embodiment of this invention, the orthopedic treatment device includes a software subsystem supporting bidirectional communication to external mobile device platforms such as Apple iOS®, Google Android®, and Microsoft Windows®. Again, the data communicated can be, and desirably is, encrypted.

In a further embodiment of this invention, the software subsystem comprises encoded software instructions on a recordable medium of the orthopedic treatment device that communicates data from sensors such as skin temperature, range of motion, and electrical impulses. The encoded software instructions on a recordable medium of the remote control device, such as described herein above, can be designed such that skin temperature at the site of the device can be displayed in degrees centigrade or Fahrenheit; electrical impulses from the muscles can be represented in a scale of 1-100, providing an indication muscle tissue health; and/or range of motion displayed in degrees on a scale of 0-360.

In a further embodiment of this invention, the software of the remote control device, such as described herein above, can be designed such that user inputs can be provided to control the orthopedic treatment device. For example, the software can be designed to provide a user interface to control the compression level applied to the joint being treated by the device; and/or increase or decrease the tension on the resistance rods.

In a further embodiment of this invention, the injury being treated by the orthopedic treatment device may involve specific types of swelling that need to be monitored via the software subsystem. For example, the swelling could be more acute on the front of the thigh and less so on the sides of the thigh and limited on the back of the thigh, this information can be mapped and allow the associated software to represent the shape of the swelling via adaptive of virtual reality software and display devices such as head gear and projection platforms and in multidimensional representations on mobile platforms, computers and smart devices such as TV sets.

6. Telemedicine Subsystem

In embodiments of this invention, the orthopedic treatment device includes a telemedicine subsystem. For example, the orthopedic treatment device and software subsystem can further include communication protocols to provide network enabled care by providing healthcare providers with access to the metrics being generated by the sensor sub-systems. These metrics include user-defined validations of high and low thresholds. The software provides for general thresholds that can be modified by the healthcare provider, where they deem closer monitoring of their patient is indicated. In a further embodiment, the metrics can be delivered via Internet infrastructure to a portal managed by the healthcare provider. The provider is able to adjust the device for compression and tension to ensure the patient is receiving the best possible remote support.

In a further embodiment of this invention, the telemedicine subsystem includes communication protocols to access NetMetCare. NetMetCare is a telemedicine interface comprising Internet communication protocols with various devices and sensors to provide remote medical care to patients, thereby avoiding office visits. It also facilitates co-operation between physicians who are able to collaborate in real-time with the patient and between themselves. The system shall notify the patient via an alert that the device's settings are being adjusted remotely for them by their doctors' office. In an aspect, NetMetCare comprises passive data acquisition from devices and sensors in contact with a subject, e.g., their skin, and further comprising, transmission of the acquired data via Internet communication protocols to a server-based platform, and further comprising a subscription-based service and interface for health care providers to provide monitoring of patients, receive alerts, provide patient feedback, and the like.

In some embodiments, the orthopedic system of this invention is embodied as footwear (e.g., a foot brace) or a footwear insert, or interchangeably, sensors placed within footwear. It is within the scope of this invention that the inserts are built into the shoe rather than placed within or are stitched within a separate sock sleeve/brace worn by the user/patient. In embodiments of this invention, one or more sensors record the load/stress at the foot of the patient so as to provide methods and means to assess the load placed on various joints in the human body. The joints to be assessed are either under consideration for treatment or currently experiencing treatment for joint pain, joint surgery, or joint replacement surgery (total and partial joint). The orthopedic footwear device can be used alone or together with other braces disclosed herein, such as for monitoring/adjusting the other (e.g., knee or hip) braces.

In embodiments of this invention, the sensors are used to detect weight patterns for non-medicinal applications and/or behavioral corrections. Without loss of generality, in addition to the medical setting as described, these inserts can likewise be used by professional and "weekend warrior" athletes striving to improve their performance. Namely, in almost any sport, understanding the mechanics of the feet plays a key role in an athlete's performance. Thus, the ability to harvest data from these sensors, throughout, for example, a marathon or golf tournament, allows trainers to measure the athlete's performance against the actual stressors in their feet, knees, and hips. With those readings, the trainers can determine if that golfer tends to slice a ball when addressing it on a downward incline. Once understood, the trainer is able to help the golfer change the incline setup and reduce a stroke or two from their game. Similarly, distance runners can improve speed by understanding the changes in the running position of their joints as fatigue sets in and larger muscles start "stepping-in" to compensate for exhausted control muscles. Succinctly, the readings provided by these inserts can redefine the way athletes and weekend warriors understand how they can improve their performance in addition to minimizing short and long term injuries.

The structure and use of the orthopedic footwear device is discussed below primarily in terms of footwear inserts for medical treatment. However, without loss of generality, the disclosed invention operates in various footwear and in the same manner to provide readings and guidance for athletic or other diagnostics.

Embodiments include the ability to measure the load in the form of the weight on an injured joint based on the weight recorded on the heel, forefoot, and/or entire foot of either and/or both feet. Thus, it is within the scope of this invention to measure readings in the foot of the leg with and/or without the injured (or repaired) joint. It is likewise within the scope of this invention to record the load, namely the weight, burdened on either or both feet of the injured leg or legs in the case of multiple injuries. The inserts may also be used to contrast a healthy limb against that of the injured or corrected joint to allow for additional analysis of the use of the corrected joint, compensation by the healthy limb, and other factors important to the treatment and care of injured and post-operative patients. Additionally, as aforementioned, the inserts may be used for sports training, and/or deeper understanding of an athlete's motion and stress characteristics.

Weight applied measurements are recorded for real-time decision making and/or later analysis using the disclosed sensors. These recorded data enable care providers to: evaluate effects of placing weight on the afflicted joints at time periods after surgery and during intervention; develop guidelines, commonly referred to as best practices, for patient care based on evidence-based actual weight sensor recorded and computed weight readings in addition to or in replacement of patient-reported outcomes only; determine proper placement/installation of an implanted device based on the proportional loads across the patient's feet promptly analyze intervention effects and user behavior to expedite recovery, for example, if the patient continues to avoid putting pressure on the joint, this could be an early indicator of potential infection, product defect, poorly implemented graft, etc.; analyze the stress point in the body and their impact on performance; develop individualized training guidelines for athletic performance enhancements; and/or develop global "best practice" guidelines generated based from readings from multiple athletes.

Figure 8:
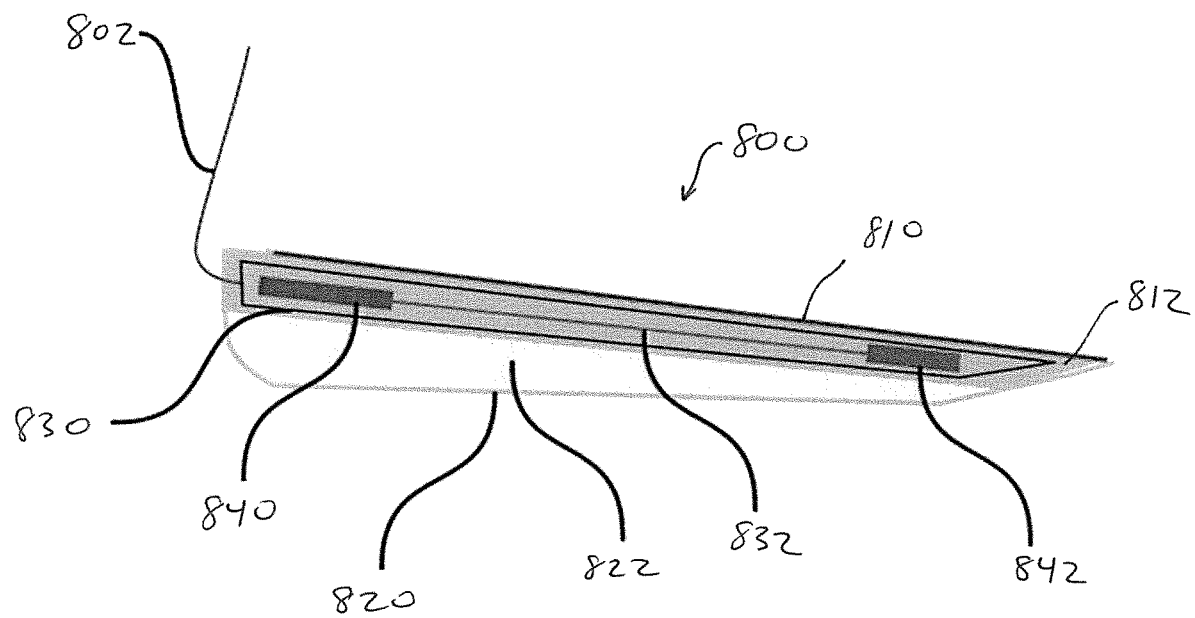
FIG. 8 illustrates an orthopedic footwear insert according to one embodiment of this invention.

FIG. 8 shows an exemplary orthopedic device according to one embodiment of this invention, which is an insert 800 that is placed into footwear, for example, a shoot or boot. In one embodiment, readings are obtained using an insert 800 connected to one or more computing devices (See, e.g., the telemedicine system in FIGS. 20-22) that receives measurement readings and can transfer instructions. Communication with the computing device occurs via wired 802 or wireless communication. Wire connection 802 can also connect to one or more other body braces, such as disclosed herein. As illustrated, the insert 800 includes an upper sole 810, a lower sole 820, comfort support and placement securing foam or air 812 in the upper sole 810, and gel 822 cushioning in the lower sole 820. As will be appreciated, various sizes, shapes, and configurations are available for the sole layers, depending on need.

In FIG. 8, the upper sole 810 encloses a load cell sleeve 830 including one or more load sensors. Wire connections 802 and 832 can provide power and/or communications. As illustrated, the cell sleeve includes a rear (heel) load sensor cell 840 (or array) and a front (forefoot) load sensor cell 842 (or array). It is within the scope of this invention to use a plurality of cell sleeves . It is within the scope of this invention to have multiple load cells and cell sleeves. The rear load sensor 840 and front load sensor 842 record the weight placed upon them, and the communication mechanisms 802 and 832 relay these readings to the computing device(s).

In embodiments of this invention, the cell load sensors measure the aforementioned weight/load utilizing wafer or nano load cells located within two micro-shells. These micro-shells are desirably held in one or more, preferably cushioned, sleeve(s) 830 used to maintain the device's position under the foot.

Figure 9:
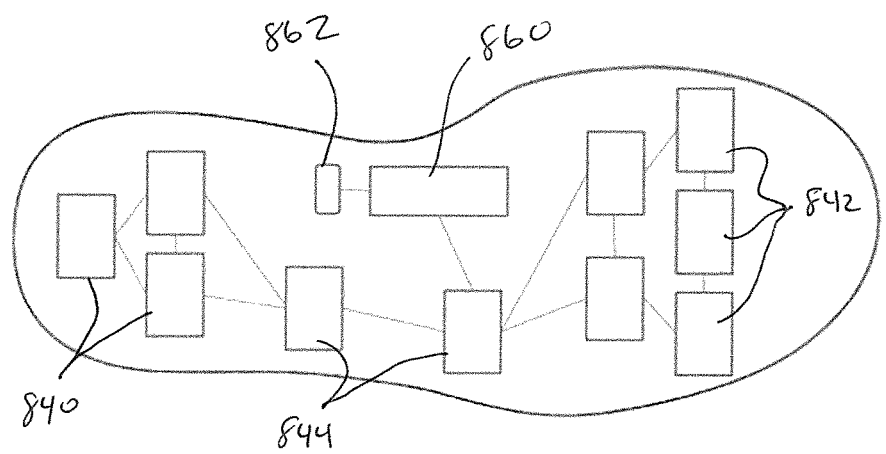
FIG. 9 shows a representative footwear insert configuration according to one embodiment of this invention.
Figure 10:
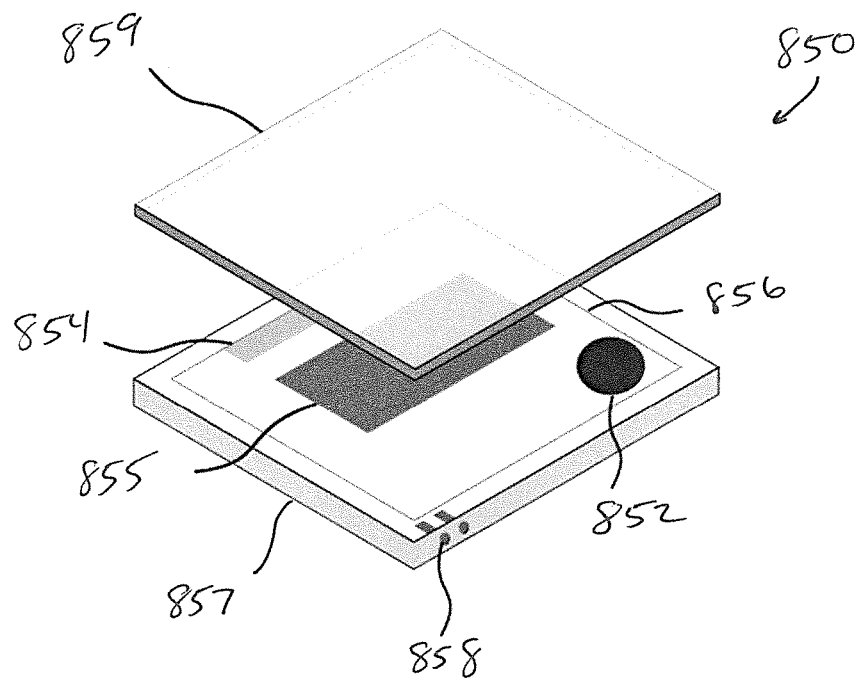
FIG. 10 shows a load sensor cell according to one embodiment of this invention.

FIG. 9 illustrates a representative array of load sensors. Three sensors 840 are located in the heel region and five sensors 842 are located in the forefoot region. Two additional sensors 844 are located along the middle foot instep arch. FIG. 10 illustrates an exemplary load cell, for use anywhere in FIG. 9, although other configurations of stress/load cells that capture similar data are likewise within the scope of this invention. Each cell 850 is powered by a battery 852. In some embodiments, rather than powering via batteries, or batteries alone, the device, including but not limited to load cells, is powered via a kinetic energy element 860 in the insert. Additionally, in one embodiment, power would be coming from the source under the arch and not within each load cell. It is also within the scope of the invention to use a combination of battery cells and power generated via kinetic energy. Using batteries simplifies the design and implementation. However, maintenance and care for the device is simplified using strictly kinetic energy. For example, reliance on kinetic energy simplifies machine washing.

The communication of readings recorded by load cell sensors 855 to the external device can be provided via a low power radio transmitter, either using a single transmitter 862 in FIG. 9, and/or in each sensor 850 as, for example, Bluetooth™ radio transmitter 854. A full perimeter surrounding antenna 856 can also be included. This communication system transmits using various communication methods known in the art, including but not limited to Bluetooth™, NFC, and other wireless networking protocols. Without loss of generality, in addition to or in the alternate, both power and communication can be accommodated via the use of wired connections using an external connector port 858. The entire cell is encased between bottom support 857 and top cover 859.

Figure 11:
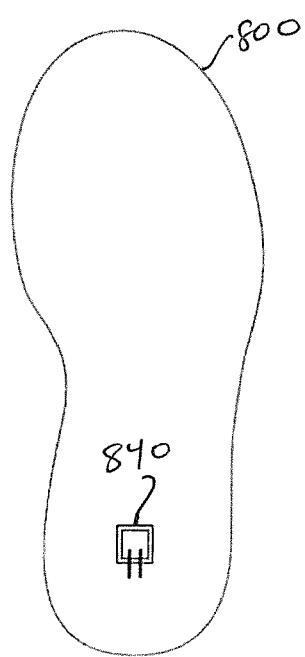
FIGS. 11-17 each show a representative sensor array according to embodiments of this invention.
Figure 12:
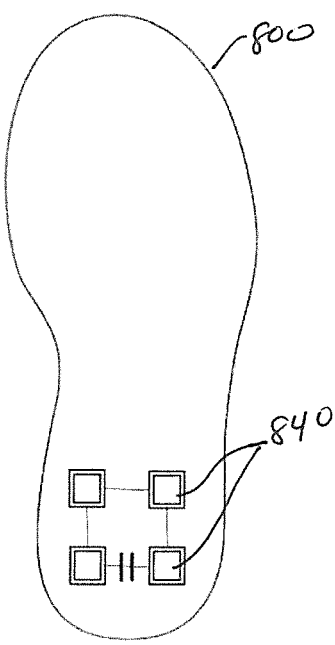
Figure 13:
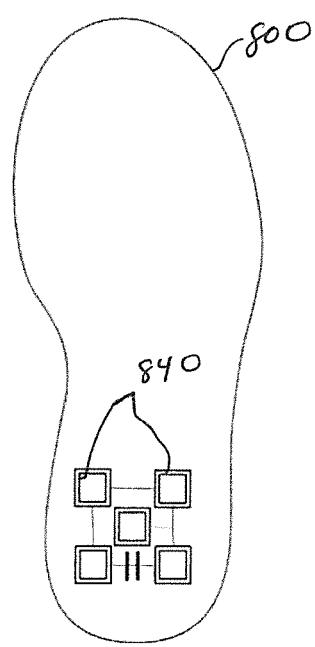

FIGS. 11-13 illustrate exemplary cell 840 arrays for the heel side of an insert. For example, without loss of generality, FIG. 11 shows a single load cell 840 that can measure the vertical force being applied to the heel. FIG. 12 shows a quad-load cell 840 array pattern that can measure the distributed load in the heal as well as the alignment of the weight across the heel. FIG. 13 shows a quint grouping of cell 840, which can measure the distribution of weight around a core vertical weight. It is within the scope of this invention to configure the heel with any number of located cells. These configured cell sensor approaches and other similarly configured cells detect, capture, store, and provide readings that indicate how the heel is sticking to the ground and whether, for example, the foot is tending to pronate or supinate. These reading, when provided to medical professionals, improve ailment, injury, surgery, and/or recovery assessment accuracy.

Figure 14:
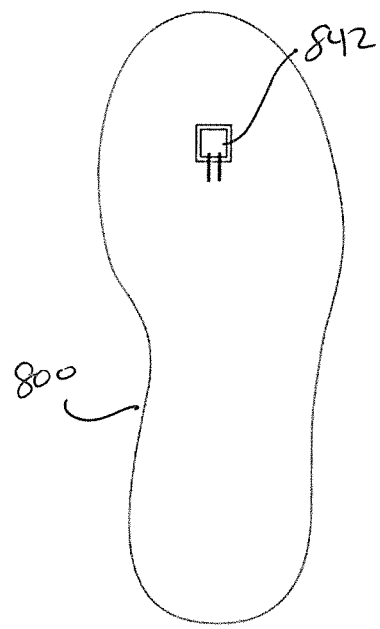
Figure 15:
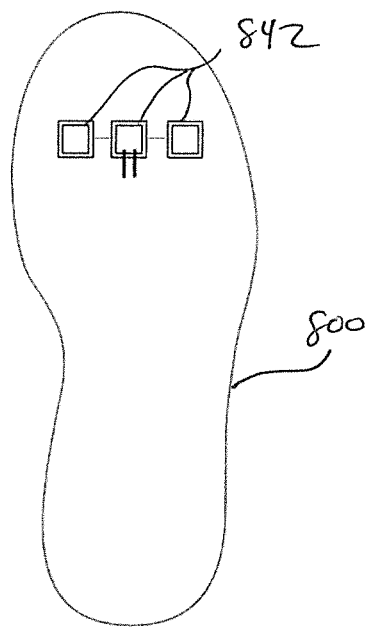
Figure 16:
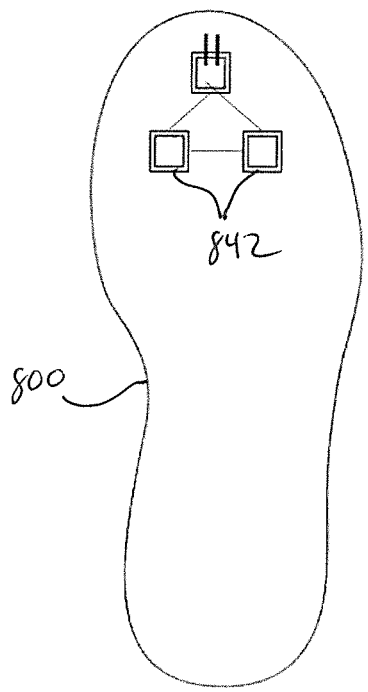
Figure 17:
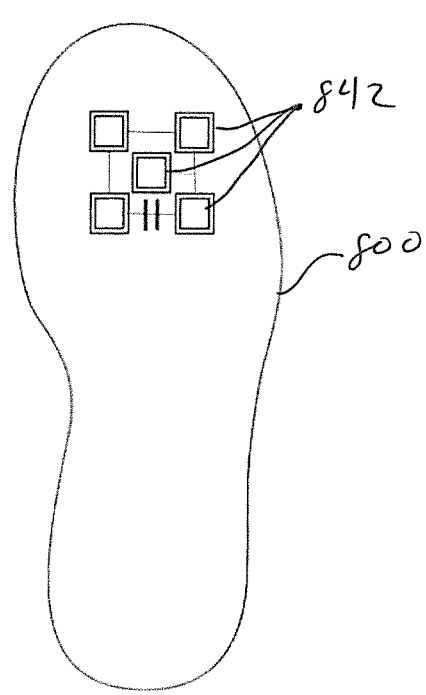
Figure 18:
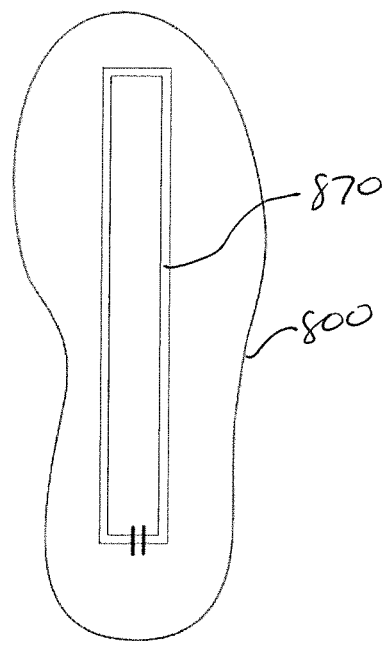
FIG. 18 shows a load sensor according to one embodiment of this invention.

FIGS. 14-17 show exemplary array patterns for cells 842 located under the patient's forefoot (e.g., the ball of the foot) each useable alone or with heel sensors. FIG. 14 shows a single load cell 842 that measures the vertical force being applied to the forefoot. FIGS. 15 and 16 show two possible configurations of a triple-array of load cells 842, which can measure the distributed load of the inner, central, and outer forefoot, as well as the alignment of the weight across the forefoot, to detect for example super and pronation of the foot and thereby the knee and hip. FIG. 17 shows a quint grouping of sensors 842, which can measure the distribution of weight across the five pressure points in the forefoot. It is within the scope of this invention to configure the forefoot with any number of located cells, with each array being able to be combined with any of the arrays of FIGS. 11-13. These configured cell sensor approaches and other similarly configured cells detect, capture, store, and provide readings that indicate way the forefoot is sticking to the ground and whether for example, the foot is tending to pronate or supinate. These readings, when provided to medical professionals, improve ailment, injury, surgery, and/or recovery assessment accuracy. It is within the scope of this invention that either or both heel and/or forefoot sensors are used. It is likewise possible to combine all sensors into one composite sensor 870, such as spanning a significant portion of the foot as shown in FIG. 18.

Figure 19:
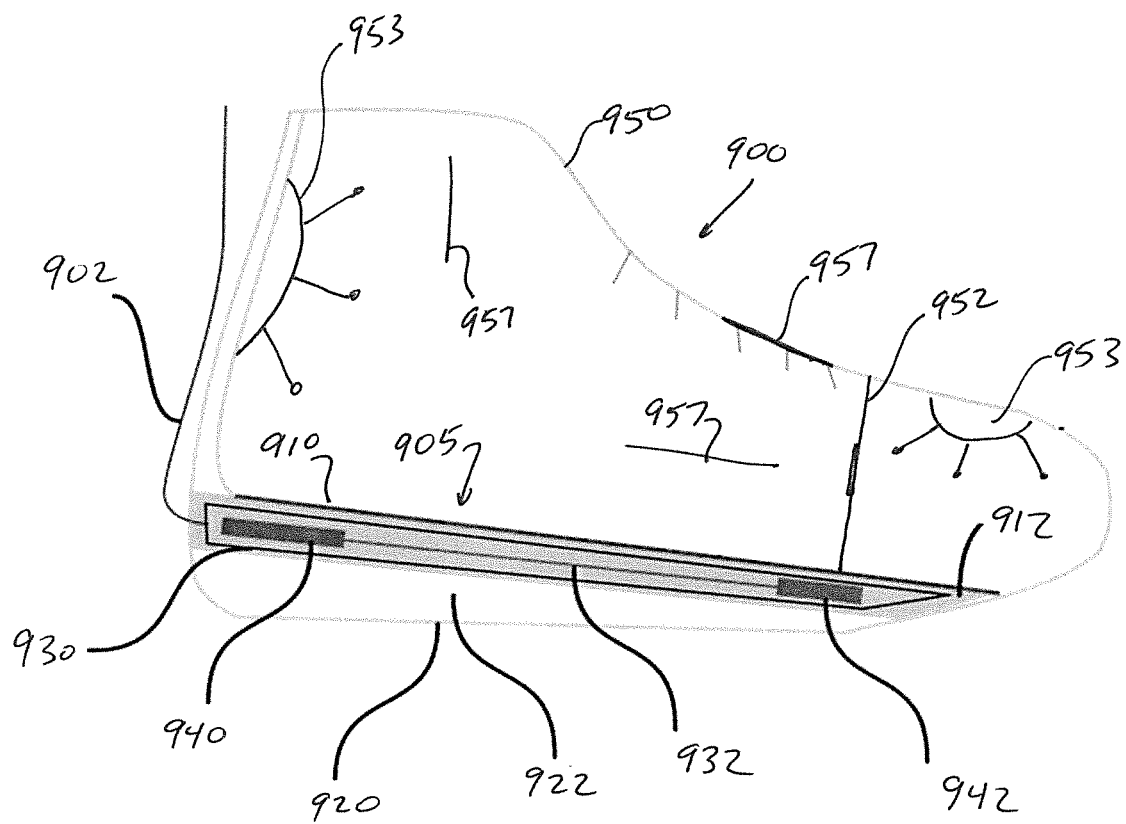
FIG. 19 shows a representative footwear brace, sleeve, and/or insert configuration according to one embodiment of this invention.

FIG. 19 shows an exemplary orthopedic device 900 according to another embodiment of this invention. The device 900 includes a footbed insert 905, such as shown in FIG. 8 further with an upper sleeve or brace 950 into which the foot is placed. The entire device can be inserted into a shoe, or the footbed can be formed as an outsole for use without a secondary shoe. As illustrated, the footbed insert 905 includes an upper sole 910, a lower sole 920, comfort support and placement securing foam or air 912 in the upper sole 910, gel 922 cushioning in the lower sole 920. Load cell sleeve 930 includes sensors 940 and 942, connected by wire 932, and wired to a power source and/or another device, such as a knee brace discussed above by wire connection 902.

The upper sleeve 950 can include any material and any sensor subsystem as discussed above for the knee or elbow brace of FIG. 1. For example, the sleeve 950 can include an assortment of sensor(s) and stimulator(s) 953 in any of multiple positions. In various aspects, these sensor(s) can measure a diversity of inputs such as moisture, electric current, and sound, as discussed above. The data signal or information derived from such inputs, like with other components in the orthopedic treatment system, can be sent via a network to the computing device for further processing. The sleeve 950 can include a flexible ring 952, such as about the foot or ankle, to detect swelling. The ring 952 can be embodied as discussed above, such as illustrated in FIG. 3. The sleeve 950 can likewise include a compression subsystem 957 that provides a tightening and loosening functionality through all or one or more sections of the sleeve 950. The compression subsystem 957 can include system components such as described above for FIGS. 4 and/or 5. The compression subsystems 957 can provide tightening across the foot, such as being placed near or about a 'shoelace' position or along a side of the sleeve, and/or about the ankle to provide ankle support, or to loosen for swelling relief.

Using the combined data recorded by the load sensor and/or arrays located at the heel and/or the forefoot, a model is generated. This model represents the loads and stresses brought to bear on, not only the foot, but on affected joints. The model generated can present its findings, such as in an application GUI using multiple forms including but not limited to: the raw data outputs, the data represented and characterized as "hot" and "cold" spots on the under surface of the foot, and/or an interpretation generated via an AI-driven analysis tool that extrapolates these data recorded to provide graphical representations of the actual loads and stresses and their distributions across the foot. These representations could likewise, without loss of generality, represent the potentially damaging stress points in other parts on the body including for example, knees, hips, and spine.

Figure 20:
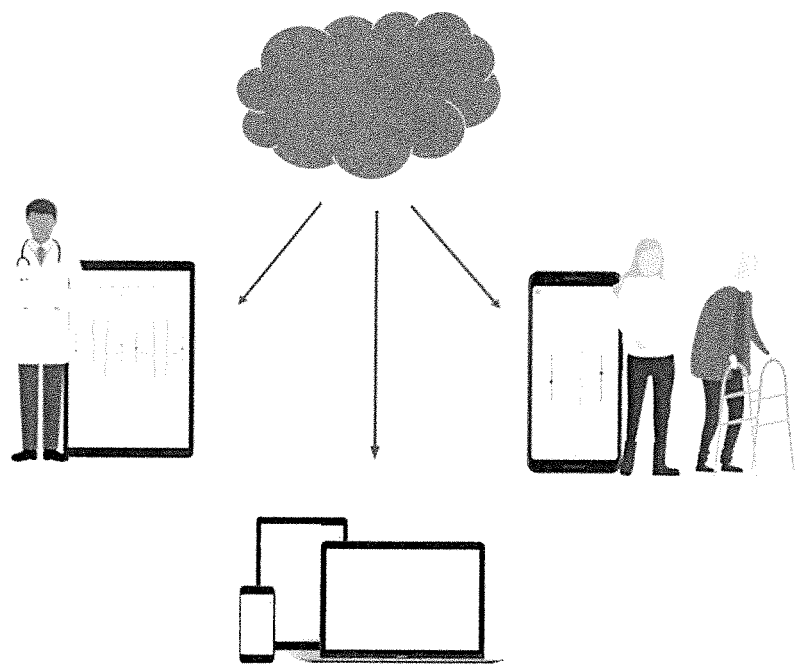
FIG. 20 shows a computing system according to one embodiment of this invention.
Figure 21:
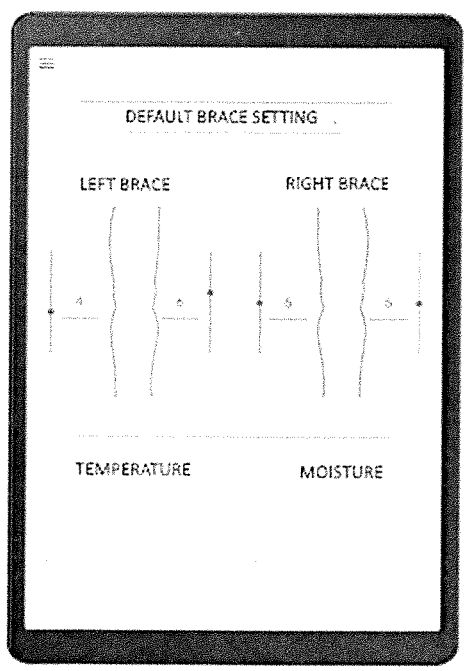
FIGS. 21 and 22 each show a mobile device user interface according to one embodiment of this invention.
Figure 22:
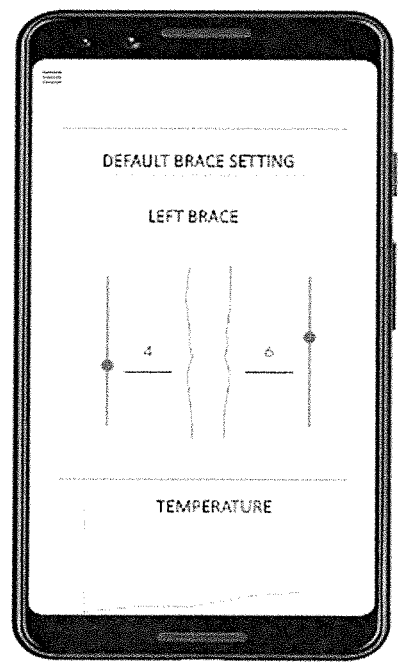

FIGS. 20-22 illustrate a use of the orthopedic device for treatment. The insert and/or other sleeve or brace can be worn by the patient, and communicate to remote electronic device, such as computers or handheld devices (e.g., a smartphone). The local or remote medical professional can monitor the weight distribution on the inserts, and make any necessary recommendation or remote adjustment to the device(s) and/or the treatment plan. FIGS. 21 and 22 are example GUIs that indicate that the left orthopedic device for a patient shows, from the sensor data, an uneven weight distribution compared to the right brace. The information, along with a recommendation from the medical professional can be provided to the patient or a physical therapist for correction. Likewise, adjustments can be made to the braces worn by the patient (e.g., a hip or knee brace), desirably from the remote application via telemedicine.

In embodiments of this invention, a calibration application can be run with or in the device or on a remotely connected smartphone-like device that requires the patient to stand on the device on a firm floor (i.e., not carpeted or padded in any way) to assess their actual weight and likewise do so when the insert is placed in the shoe or other brace. The calibration application will assess the difference in weight in the patient on the sleeve(s) alone versus the measurements once in the brace. This assessment uses data from the various types of available load cells to calculate the required offset for the use of the device by each individual patient making the device specific to the needs of that patient. Note that this calibration is needed for each patient and each brace or shoe configuration to improve accuracy and customize the patient specific—brace specific processing.

In yet another embodiment, the network of inserts interact with the remote device. In such an embodiment, communication is collected by a user device, such as a smartphone, connected to the sensor network via a low powered network, such as the device's "hotspot". Via the smartphone, the readings are transferred for processing to a remote storage and processing facility, such as "the cloud", and the appropriate caretaker(s) (e.g., physician or trainer), can receive the corresponding readings and/or analysis.

Figure 23:
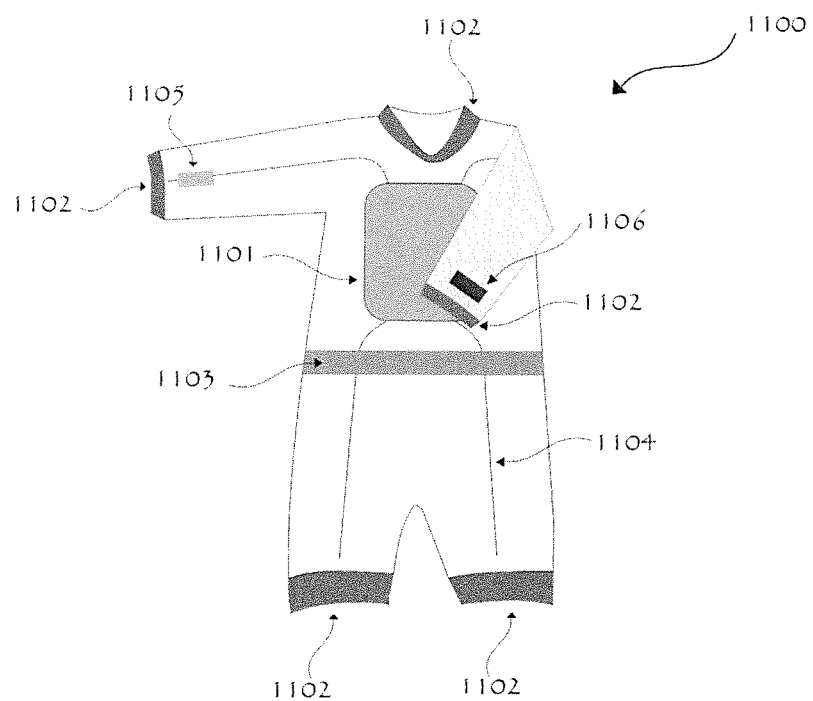
FIG. 23 illustrates an infant body suit with the left arm attached to the center of the body.

FIG. 23 shows a sleeve according to embodiments of this invention embodied as a body suit, and particularly an infant body suit 1100. The sleeve or body suit has an interior cavity for receiving the patient or infant body. The body suit 1100 includes a torso section and two arm sleeve sections and two leg sleeve sections, and could alternatively be embodied, for example, simply as a shirt without leg sleeve sections, arm/leg sections only, or a onesie without arm or leg sleeve sections, depending on need.

The body suit includes a pad 1101 in the center of the body suit 1100. This pad 1101 desirably includes one or more micro-charging units that generate and store sufficient power to power the various sensors in the body suit 1100 discussed below. The needed power is generated via a combination of, for example, infant body heat and breathing motion, both converted to energy. As only minimal energy is needed to operate the sensors incorporated in the suit 1100, the energy stored in the microcells within the pad 1101 generally suffices. It is within the scope of this invention that alternate micro power mechanisms known in the art can be used to power the suit components.

The body suit 1100 includes a sensor subsystem including at least one sensor integrated with the sleeve or suit, and configured to detect breathing motion of the body and/or oxygen levels in the body. Suitable sensors include motion, temperature, moisture, pulse, circumferential strain gauges, and/or blood oxygen (e.g., SpO2) sensors. The sensors can be distributed as needed throughout the suit, such as included as cuff sensors 1102 and/or waist sensors 1103 located on the cuffs (neck, ankle, and/or wrist) and waist, respectively. In some embodiments of this invention only some of these sensors are present. In some embodiments of this invention replications of one or more of these sensors are present. Power is provided to these sensors via wiring 1104 inlaid and distributed across the body suit 1100 as needed.

Figure 24:
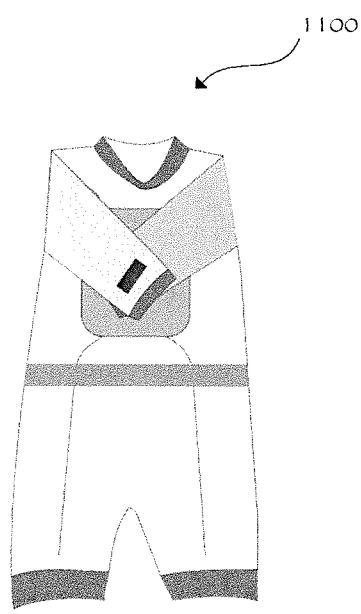
FIG. 24 illustrates an infant body suit with the right arm attached over and to the left arm sleeve.

In some embodiments of this invention, adhesives or fasteners 1105, such as but not limited to hook and loop fasteners (Velcro®), snaps, etc., are attached to both sides of the arm sleeves to secure the arms to the chest. Initially, one arm, as shown in FIG. 23, can be attached to the pad 1101 using the inner fastener 1105 of the arm, and then the inner fastener 1105 of the other arm can be attached to an outer fastener 1106 of the first arm, as shown in FIG. 24. Desirably, either arm can be attached to the pad 1101 and to each other. Thus, the right or the left arm can be placed underneath the other and attached to the pad 1101. It is also within the scope of this invention for both arms to be directly connected via their respective inner fasteners 1105 to the pad 1101.

The sensors of the body suit 1100 desirably communicate via a local, low-powered network, such as, but not limited to Bluetooth®, with a startle mechanism configured to actuate upon a detection of a predetermined event that indicates an issue with the patient or infant. The predetermined event typically is selected from slowed or stopped breathing and/or an oxygen level below a predetermined amount. The system can also monitor for other potential issue-indicating events known in the art, and used for a startle mechanism, depending on need. The startle mechanism can include any one or more of various physical startling techniques to awaken, either partially or fully, the patient or infant. Exemplary startle mechanisms include, without limitation, an agitating component or support, an audio stimulation (e.g., speaker subsystem), an electrical stimulation, a temperature stimulation, a pressurized air stimulation, or combinations thereof. The system typically includes a controller, separate to or integrated with the sensor subsystem or startle mechanism, for controlling these components and the communication there between.

In embodiments of this invention, the startle mechanism, desirably along with any controller, is incorporated within or otherwise in combination with a patient support configured to support the patient or infant body thereon. In some preferred embodiments of this invention, the patient support agitates the body thereon upon the detection of the predetermined event. The agitation can be, without limitation, a vibration, such as from a vibrating support or component, and/or a drop component, such as the drop platform configured to support the body and drop suddenly in a controlled manner upon the detection of the predetermined event. The support can alternatively or additionally include a speaker system for an audio startle stimulation. These, or other startle mechanisms, can be used in various combinations, for example, at the same time or sequentially, such as in increasing intensity.

Embodiments of the patient support of this invention include a drop platform as a startle mechanism. Via a communications port, a controller housed in the platform receives and monitors in real-time all sensor readings and determines if a response is needed. If deemed necessary, the controller initiates a platform drop and triggers any and/or all auxiliary startle mechanisms (sound, temperature, pricks, forced air, etc.) as described hereafter.

Figure 25:
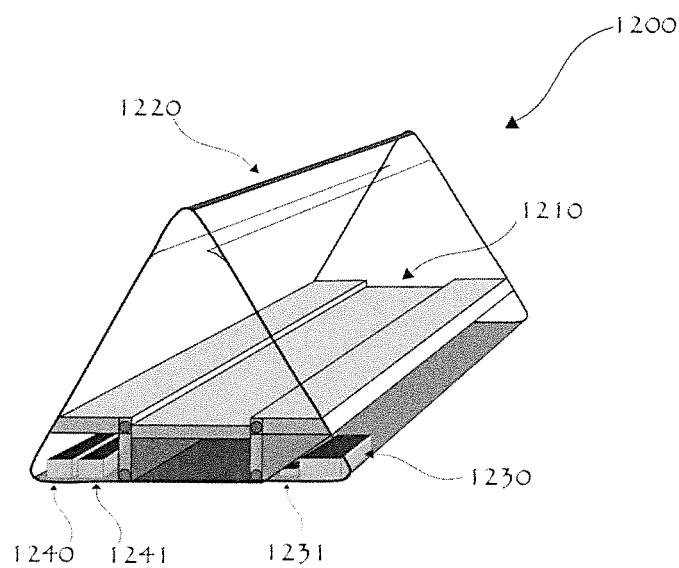
FIG. 25 illustrates a SIDS prevention encasement, according to one embodiment of this invention.

FIG. 25 generally illustrates a SIDS prevention encasement 1200, according to one embodiment of this invention. The encasement 1200 includes a drop platform 1210. The devices includes the necessary power related components, such as an A/C power outlet box 1230, where a power chord is stored when not in use, a power source 1231, a backup battery power source 1241, and a backup battery charger 1240. The enclosure further includes a speaker panel 1220, as an alternative or additional startle mechanism.

The drop platform 1210, upon detection of need, rapidly drops to startle and awaken the infant placed thereon. The speakers 1220 can additionally blast loud sounds, preferably in a seemingly flowing and moving pattern, that likewise scare and awaken the child. Both the loud noise and the sudden drop serve as startle mechanisms to startle and awaken the infant, instinctively forcing the infant to cry and ingest air.

Figure 26:
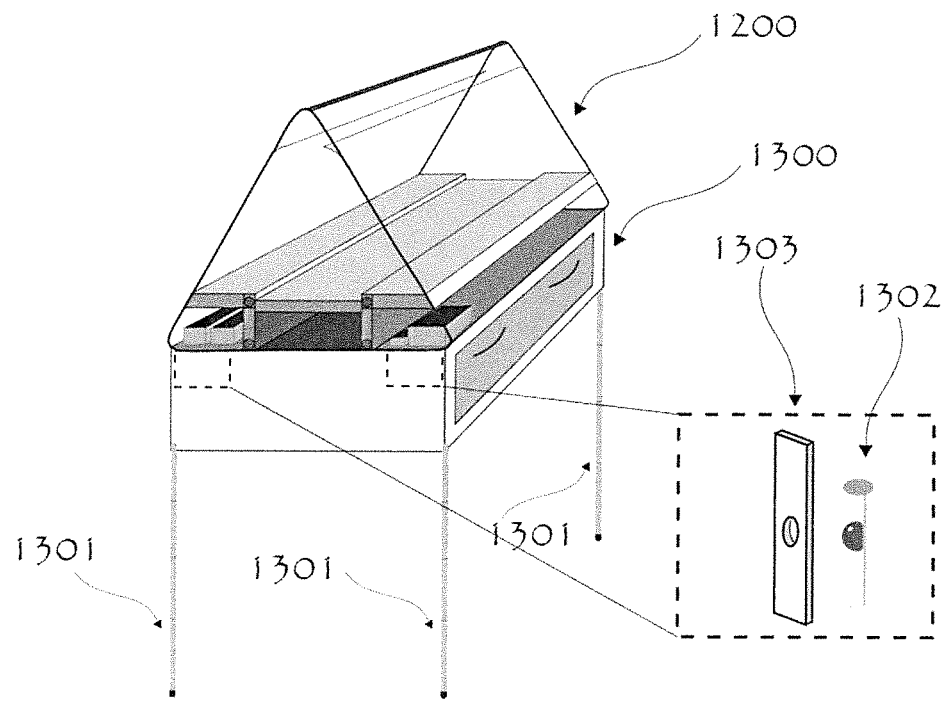
FIG. 26 shows the encasement on a stand according to one embodiment of the invention.
Figure 27:
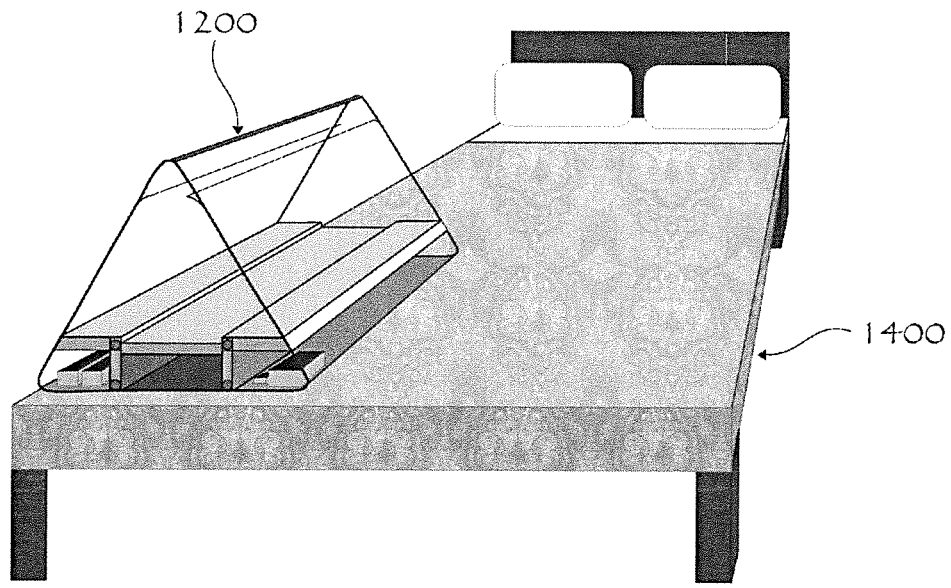
FIG. 27 shows an encasement resting on a bed.

FIG. 26 illustrates an encasement 1200 resting on top of a stand 1300. As shown, the encasement 1200 is secured via a metal hole joint 1303 built into the stand 1300, which connects to a metal ball 1302 that is part of the folding short legs of the encasement 1200. The stand legs 1301 are preferably adjustable as shown in FIG. 13, providing the caregiver easier access and greater convenience. As shown, the encasement 1200 is self-contained; hence portability, namely removal from the resting base 1300 is provided by preferred embodiments. For example, the self-contained encasement 1200 can likewise be placed on top of a bed 1400, as shown in FIG. 27.

Figure 28:
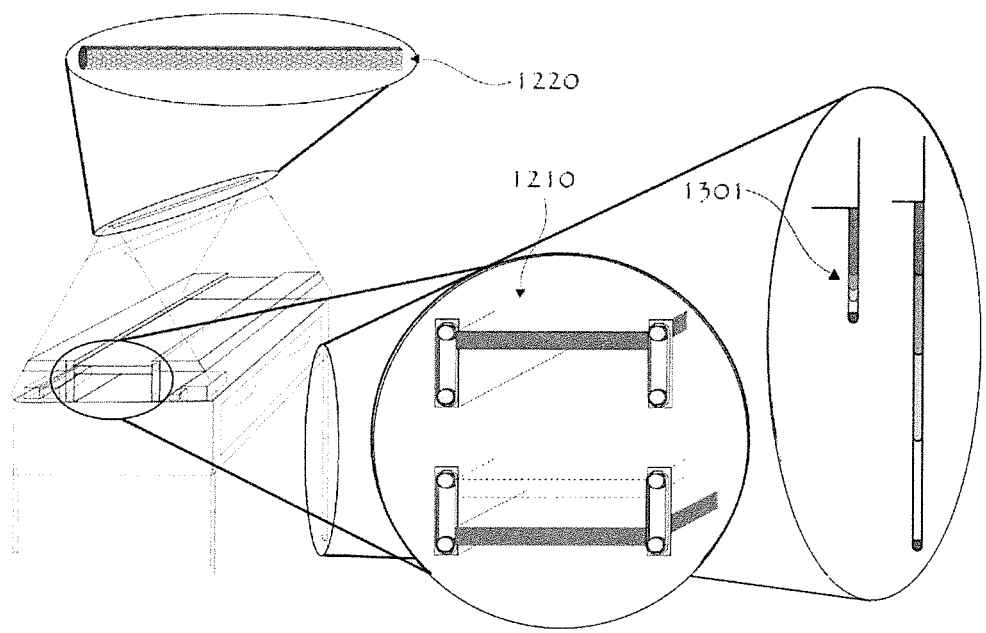
FIG. 28 illustrates components of an encasement, according to one embodiment of this invention.
Figure 33:
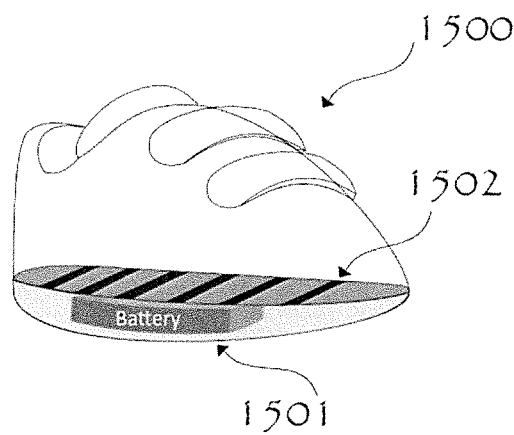
FIGS. 33-36 each show a shoe startle mechanism, according to one embodiment of this invention.
Figure 34:
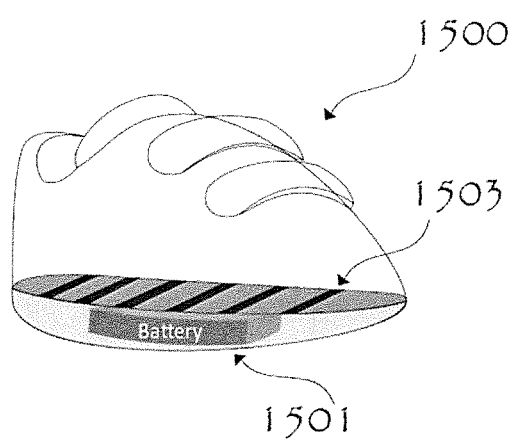
Figure 35:
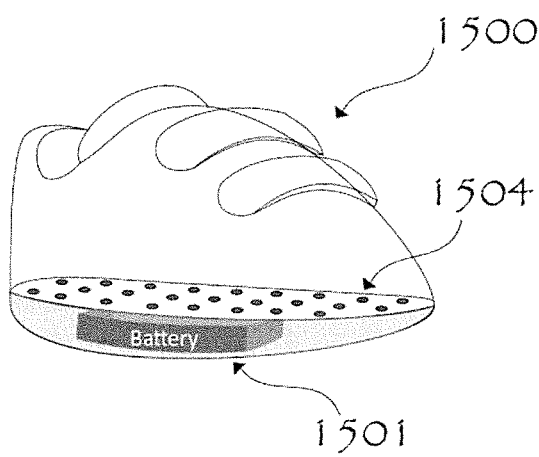

Exemplary components of a SIDS prevention encasement 1200 according to embodiments of this invention are illustrated in FIG. 28. As illustrated, a graphite speaker is used as the speaker panel 1220, but other speaker options known in the art, such as but not limited to a set of linearly arranged speakers, are likewise within the scope of this invention. A desirable effect the speaker panel 1220, according to embodiments of this invention, is to produce a blast of loud sounds in a seemly flowing and moving pattern. FIG. 28 also illustrates possible positions of the drop platform 1210 according to embodiments of this invention. Initially, the child is placed on the platform 1210, such as at an inclining position. The degree of the incline must be sufficiently high to support a sudden drop but not too high as to result in the infant sliding down the incline. Upon the controller determining that it is necessary to awaken the infant, the platform 1210 rapidly drops, startling and awakening the infant as intended. Simultaneously, loud sounds from the speaker panel 1220 can commence. Loud sounds likewise indirectly notify the infant caregiver of a potential problem.

Care must be taken to properly design the rapidly dropping platform 1210, because too harsh of a landing could harm the child. FIGS. 29 and 30 show a pulley 1214, controlled by the controller that allows the drop platform 1210 to provide a soft landing. As shown in FIG. 29, the platform 1210 is designed to fall at a non-limiting exemplary rate of 30.5 meters per second until a predetermined height. At that height, indicated as the start of the break zone, the pulley 1214 driving the drop rapidly decelerates to nearly a complete stop leading the platform 1210 to a gentle rest on the base of the encasement 1200. The initially inclined and the post-drop resting positions of the drop platform 1210 are representatively illustrated in FIGS. 29 and 30.

FIG. 31 shows a motor 1211, gearbox 1212, and drive shaft 1213 for driving and controlling the pulley 1214 system as dictated by the controller. The motor 1211 is programmed to rapidly accelerate and rapidly decelerate the gearbox 1212 rotating the shaft 1213 so as to create a rapid drop and a comfortable landing for the drop platform 1210 once it is determined by the controller that a drop is needed.

FIG. 32 illustrates an end view of a SIDS prevention encasement 1200, according to embodiments of this invention. An optional fan system 1252 prevents potential carbon dioxide buildup by the infant's face. By inducing air circulation within the encasement 1200, particularly a partially or fully enclosed encasement, the potential for residual carbon dioxide is reduced. As shown, fans 1252 inserted into the openings in the front panel 1250 are powered by motor 1251. Vent openings in the sides and/or opposing end of the encasement 1200 enable the flow of air out of the encasement 1200. Variable positioned slits 1253 further support air circulation.

Alternative or additional startle mechanisms can be included to interact with the body sleeve system to awaken the infant and thereby prevent SIDS. Embodiments of this invention include mechanisms incorporated in a wearable item, such as integrated within the sleeve itself, a separate clothing item, and/or a footwear apparatus. FIGS. 33-36 each illustrate a footwear (e.g., shoe) startle mechanism according to embodiments of this invention. These shoes 1500 awaken the child by, for example, an electrical stimulation mechanism, a temperature stimulation mechanism, a pressurized air stimulation mechanism, or combinations thereof. As shown, these approaches all rely on shoes added to or in combination with the body sleeve 1100 of FIG. 23. Although annoying to the infant, hence providing an awakening event, none of these prescribed approaches actually harm the infant as their dosages are low and their direct contact with the infant is protected.

Each of FIGS. 33-36 shows a view an infant awakening shoe 1500. Multiple instantiations of such shoe 1500 exist. In all embodiments presented, a power source 1501, herein represented by a non-limiting example of a battery 1501, is needed to activate an annoying, and hence awakening, substrate 1502-1505, for example, as the side/top and/or sole of the shoe 1500. A controller within the shoe 1500 communicates with the main controller in the infant body suit 1100, triggers an awakening response when needed.

Figure 36:
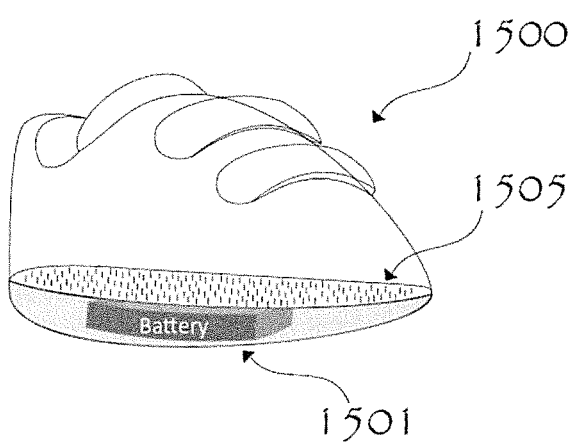

In one embodiment, if deemed necessary, the infant is awakened via mild electric impulses or shocks. These shocks are similar but not limited to those potentially delivered by a 9 Volt DC battery. The mild shocks are introduced to both feet via the electrically stimulated bars 1502 within the shoe 1500 shown in FIG. 33. In another embodiment, instead of introducing an electric shock to both feet, a sudden cold of freezing temperature is introduced. The sudden freezing is introduced via icing temperature bars 1503 in FIG. 34. In yet another embodiment, instead of introducing an electric shock or freezing temperatures to both feet, sudden pricks via pressurized compressed air through vent holes 1504 in FIG. 35 or built in pins 1505 in FIG. 36 are introduced. All of these approaches awaken the infant, yielding the desired effect. Likewise within the scope of this disclosure is combining multiple of these stimulants into a single shoe.

Thus the invention provides various embodiments of body supports, monitoring, and/or treatment devices and systems. The incorporation of various sensors or other active systems provide improved treatment, which can be monitored and controlled locally or remotely.

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A support and/or treatment system, comprising:
   an orthopedic footbed adapted to be worn by a patient;
   a footbed sensor integrated with the orthopedic footbed, and configured to measure a load and/or weight thereon;
   a knee support brace adapted to be worn by the patient;
   a control unit including a processor integrated with the knee support brace;
   a telemedicine control device remote from the orthopedic footbed and the knee support brace, and connected to the footbed sensor and the control unit over a network, wherein the telemedicine control device is configured to measure and model stress in a foot, knee, and/or hip of the patient;
   an adjustment mechanism integrated with the knee support brace, wherein the control unit is in controlling combination with the adjustment mechanism, and the adjustment mechanism comprises a compression subsystem integrated with the knee support brace and having variable tension controllable by the telemedicine control device via the control unit, the compression subsystem comprises: a rotating bar or rod and a motor configured to rotate the rotating bar or rod to adjust a compression or tension in the knee support brace, and a plurality of straps each connected at a first end to the rotating bar or rod and fixed at a second end to the knee support brace, wherein rotation of the rotating bar or rod tightens or loosens the plurality of straps to adjust compression of the knee support brace about an internal cavity of the knee support brace;

a sensor subsystem integrated with the knee support brace and in communication with the control unit, wherein the compression or tension is automatically monitored by the sensor subsystem and automatically adjustable by the control unit, and wherein the sensor subsystem comprises a first flexible ring integrated with the knee support brace, encircling the internal cavity of the knee support brace, and with at least one sensor adapted to measure swelling in a body part within the first flexible ring and the knee support brace; and wherein the telemedicine control device is accessible by a remotely located telemedicine healthcare provider to receive metrics from the footbed sensor and the control unit and for control and adjustment of the adjustment mechanism and the knee support brace throughout treatment of the patient by the telemedicine healthcare provider via the knee support brace.

2. The system of claim 1, wherein the footbed sensor comprises an array of load cells in at least one of a heel location or a forefoot location of the orthopedic footbed.

3. The system of claim 2, wherein the array of load cells comprises a quint array including four corner load cells about a center load cell.

4. The system of claim 1, further comprising a low power wireless transmitter disposed within the orthopedic footbed, and in communication with the telemedicine control device.

5. The system of claim 4, wherein the low power wireless transmitter is configured to send readings to a connected smartphone and the smartphone comprising an application that stores readings locally and transmits the readings to a remote cloud server.

6. The system of claim 1, further comprising a power subsystem integrated with the orthopedic footbed, and comprising a kinetic energy source configured to generate power from movement of the orthopedic footbed.

7. The system of claim 1, wherein the orthopedic footbed comprises a footbed brace or a sleeve configured to extend about a foot of the patient.

8. The system of claim 7, further comprising a further sensor subsystem integrated with the orthopedic footbed or the footbed brace or the sleeve, and in communication with the telemedicine control device, wherein the sensor subsystem comprises a pulse sensor, a blood flow sensor, a blood pressure sensor, an oxygen sensor, a temperature sensor, an electric sensor, a moisture sensor, a biological/chemical sensor, a range of motion sensor, a compression/resistance sensor, a circumferential strain gauge, or combinations thereof.

9. The system of claim 8, wherein the sensor subsystem comprises the electric sensor configured to determine muscular micro-electrical activity.

10. The system of claim 8, wherein the sensor subsystem comprises a flexible ring integrated with the footbed brace or sleeve and configured to be disposed about the foot, and at least one sensor adapted to measure swelling in the foot within the ring.

11. The system of claim 7, further comprising a compression subsystem integrated with the footbed brace or the sleeve and having variable tension controllable by the telemedicine control device via the control unit.

12. The system of claim 11, wherein the compression subsystem comprises a rotating rod and a motor configured to rotate the rotating rod to adjust a compression or tension in the footbed brace or the sleeve.

13. The system of claim 12, wherein the compression or tension is automatically monitored by the sensor subsystem and automatically adjustable by the telemedicine control device.

14. The system of claim 11, further comprising:
a rotatable footbed rod including a flexible center section between two rigid end sections; and
a plurality of footbed straps each connected at a first end to the rotating footbed rod and fixed at a second end to the compression subsystem, wherein rotation of the bar tightens or loosens the footbed straps.

15. The system of claim 1, wherein the telemedicine control device communicates with the footbed sensor through the control unit of the knee support brace.

16. A support and/or treatment system, comprising:
a first orthopedic device comprising a knee support brace or sleeve adapted to be worn by a patient;
a control unit including a processor integrated with the first orthopedic device;
a telemedicine control deviceremote from the first orthopedic device and connected to the control unit over a network;
an adjustment mechanism integrated with the first orthopedic device, wherein the control unit is in controlling combination with the adjustment mechanism, and the adjustment mechanism comprises a compression subsystem integrated with the first orthopedic device and having variable tension controllable by the telemedicine control device via the control unit, the compression subsystem comprises: a rotating bar or rod and a motor configured to rotate the rotating bar or rod to adjust a compression or tension in the first orthopedic device, and a plurality of straps each connected at a first end to the rotating bar or rod and fixed at a second end to the knee support brace or sleeve, wherein rotation of the rotating bar or rod tightens or loosens the plurality of straps to adjust compression of the knee support brace or sleeve about an internal cavity of the knee support brace or sleeve;
a sensor subsystem integrated with the first orthopedic device and in communication with the control unit, wherein the compression or tension is automatically monitored by the sensor subsystem and automatically adjustable by the control unit, and wherein the sensor subsystem comprises a first flexible ring integrated with the first orthopedic device, encircling the internal cavity of the knee support brace or sleeve, and with at least one sensor adapted to measure swelling in a body part within the first flexible ring and the first orthopedic device;
a second orthopedic device comprising an orthopedic footbed adapted to be worn by a patient;
a footbed sensor integrated with the orthopedic footbed, and configured to measure a load and/or weight thereon, wherein the telemedicine control device is remote from the second orthopedic device and connected to the footbed sensor over the network;
wherein the telemedicine control device is accessible by a remotely located telemedicine healthcare provider to receive metrics from the control unit and the footbed sensor, and for control and adjustment of the adjustment mechanism and the first orthopedic device throughout treatment of the patient by the telemedicine healthcare provider via the first orthopedic device.

\* \* \* \* \*